(12) United States Patent
Taugerbeck et al.

(10) Patent No.: US 7,648,742 B2
(45) Date of Patent: Jan. 19, 2010

(54) DIFLUOROSUBSTITUTED HETEROCYCLIC COMPOUNDS AND THE USE THEREOF IN THE FORM OF COMPONENTS IN LIQUID CRYSTALLINE MEDIA

(75) Inventors: Andreas Taugerbeck, Darmstadt (DE); Melanie Klasen-Memmer, Heuchelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/572,759

(22) PCT Filed: Jul. 5, 2005

(86) PCT No.: PCT/EP2005/007221

§ 371 (c)(1),
(2), (4) Date: Nov. 26, 2007

(87) PCT Pub. No.: WO2006/012965

PCT Pub. Date: Feb. 9, 2006

(65) Prior Publication Data

US 2008/0071097 A1    Mar. 20, 2008

(30) Foreign Application Priority Data

Jul. 29, 2004   (DE) ................. 10 2004 036 831

(51) Int. Cl.
*C09K 19/32* (2006.01)
*C09K 19/34* (2006.01)
*C09K 19/30* (2006.01)
*C07D 311/04* (2006.01)
*C07D 307/78* (2006.01)

(52) U.S. Cl. .............. 428/1.1; 252/299.61; 252/299.62; 252/299.63; 549/403; 549/406; 549/428; 549/462; 549/469

(58) Field of Classification Search ............ 252/299.61, 252/299.62, 299.63; 428/1.1; 549/406, 408, 549/403, 428, 462, 469
See application file for complete search history.

(56) References Cited

U.S. PATENT DOCUMENTS

| | | | |
|---|---|---|---|
| 5,414,006 A | 5/1995 | Rendenbach-Mueller et al. | |
| 5,849,217 A | 12/1998 | Nakamura et al. | |
| 6,099,759 A | 8/2000 | Chan | |
| 7,247,355 B2 * | 7/2007 | Sagou et al. | 428/1.1 |
| 2005/0247910 A1 | 11/2005 | Sugiura et al. | |
| 2006/0177603 A1 | 8/2006 | Taugerbeck et al. | |

FOREIGN PATENT DOCUMENTS

| | | |
|---|---|---|
| DE | 199 09 760 A1 | 10/1999 |
| DE | 10 2004 053279 A1 | 6/2005 |
| EP | 0594036 A1 | 4/1994 |
| EP | 0 666 262 A | 8/1995 |
| EP | 0 916 715 A | 5/1999 |
| EP | 1 491 612 A | 12/2004 |
| JP | 06256339 A | 12/1994 |
| JP | 07145371 A | 10/1995 |
| WO | WO 2004/076438 A | 9/2004 |

OTHER PUBLICATIONS

Zajc et al., "Fluorination with xenon difluoride. 37. Room-temperature rearrangement of aryl-substituted ketones to difluoro-substituted ethers", J. Organic Chem. (1990), 55(3), 1099-102.*
Caplus 1980: 408059.*
Caplus:1980:639150.*
Caplus 1974:522749.*
Bailey, J. et al., Hexafluorobenzo 'b!furan, Tetrahendron Letters, Teleay, 1975 pp. 0040-4039.
Database Caplus, Chemical Abstract Service, Columbus Ohio, Kashkoviski, O. D. et al., The Nature of Electronic Transitions In Coumarin, 3-Arylcoumarins and Their Sulfur-Containing Analogs, pp. 58-64, 70(5-6).
Database Caplus, Online, Chemical Abstracts Service, Columbus OH, Lokshin, V.A. et al, Photo-and Thermochromic Spiropyrans of the Dithiolane Series, 1980, pp. 47-50.
Database Caplus Online, Chemical Abstracts Service, Columbus Ohio, Derocque, Jean Luc et al, Asturdy of the Mass Spectrographic fragmentation of benodithioline spiropyrans, 1978.
Zajc, Barbara et al., Fluorination with Xenon Difluoride. 37. Room-temperature rearrangement of aryl-substituted Ketones to Difluoro-Substituted Ethers, Journal fo Organic Chemistry,1990, pp. 1099-1102 55(3).

* cited by examiner

*Primary Examiner*—Shean C Wu
(74) *Attorney, Agent, or Firm*—Millen, White, Zelano, Branigan, P.C.

(57) ABSTRACT

The invention relates to compounds of formula (I), wherein a, b, c, d, e, $R^1$, $R^2$, $A^1$, $A^2$, $A^3$, $A^4$, $Y^1$, $Y^2$, $Y^3$, $Z_1$, $Z^2$, $Z^3$, $Z^4$ and ═ are such as defined in claim 1, to a method for the production thereof, intermediates for the production and the thereof in the form of components in liquid crystalline media and to electrooptic display elements containing said liquid crystalline media.

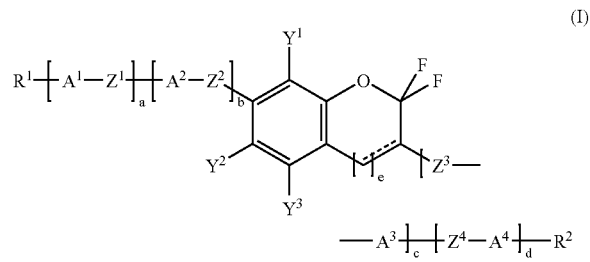

15 Claims, No Drawings

DIFLUOROSUBSTITUTED HETEROCYCLIC COMPOUNDS AND THE USE THEREOF IN THE FORM OF COMPONENTS IN LIQUID CRYSTALLINE MEDIA

The present invention relates to difluorosubstituted heterocyclic compounds, a process for their preparation, intermediate compounds for a process for their preparation, their use as components in liquid crystalline media and electrooptical display elements which comprise these liquid crystalline media. In particular, the invention relates to difluoro substituted heterocyclic compounds having negative dielectric anisotropy.

Liquid crystals have found a wide field of application since the first commercially usable liquid crystalline compounds were found approximately 30 years ago. Known areas of application are, in particular, indicator displays for timepieces and pocket calculators and large display panels, such as are used in railroad stations, airports and sports arenas. Further areas of application are displays of portable computers and navigation systems and also television and video applications. High demands on switching times and the contrast of the images are made, in particular for the last-mentioned applications.

The spatial arrangement of the molecules in a liquid crystalline medium causes many of its properties to be direction-dependent. Of importance for use in liquid crystal displays here are, in particular, the anisotropies in the optical, dielectric and electromechanical behavior. Depending on whether the molecules are oriented with their longitudinal axes perpendicular or parallel to the two plates of a capacitor, this has a different capacity; the dielectric constant $\in$ of the liquid crystalline medium is thus of different sizes for the two orientations. Substances whose dielectric constant on perpendicular orientation of the molecular longitudinal axes to the condenser plates is greater than on parallel arrangement are designated as dielectrically positive. In other words: the dielectric constant $\in_\|$ parallel to the molecular longitudinal axes is greater than the dielectric constant $\in_\perp$ perpendicular to the molecular longitudinal axes, thus the dielectric anisotropy $\Delta\in=\in_\|-\in_\perp$ is greater than zero. Most liquid crystals which are used in conventional displays come into this group.

For dielectric anisotropy, both the polarizability of the molecule and permanent dipole moments play a role. On applying a voltage to the display, the longitudinal axis of the molecules is aligned such that the greater of the dielectric constants is effective. The strength of the interaction with the electric field depends in this case on the difference between the two constants. In the case of small differences, higher switching voltages are necessary than in the case of large ones. By means of the incorporation of suitable polar groups, such as, for example, of nitrile groups or fluorine, into the liquid crystal molecules a wide range of working voltages can be realized.

In the case of the mesogenic or liquid crystalline molecules used in the conventional liquid crystal displays, the dipole moment oriented along the molecular longitudinal axis is greater than the dipole moment oriented perpendicularly to the molecular longitudinal axis. The orientation of the greater dipole moment along the longitudinal axis of the molecule also determines the orientation of the molecule in a liquid crystal display in the field-free state. In the case of the most widespread TN cells (derived from "twisted nematic"), a liquid crystalline layer only approximately 5 to 10 µm thick is arranged between two plane-parallel glass plates, onto which in each case is evaporated an electrically conductive, transparent layer of tin oxide or indium-tin oxide (ITO) as an electrode. Between these films and the liquid crystalline layer is situated a likewise transparent orientation layer, which usually consists of a plastic (e.g. polyimides). It serves to bring the longitudinal axes of the adjacent crystalline molecules into a preferred direction by means of surface forces, such that in the voltage-free state they lie flat on the inside of the display surface uniformly with the same orientation or with the same small tilt angle. On the outside of the display, two polarization films which only allow linearly polarized light to enter and emerge are applied in a specific arrangement.

Using liquid crystals in which the greater dipole moment is oriented parallel to the longitudinal axis of the molecule, very efficient displays have already been developed. Here, mixtures of 5 to 20 components are usually used in order to achieve an adequately wide temperature range of the mesophase and also short switching times and low threshold voltages. The strong viewing angle dependence, however, still causes difficulties in liquid crystal displays such as are used, for example, for laptops. The best image quality can be achieved when the surface of the display is perpendicular to the viewing direction of the observer. If the display is tilted relative to the direction of observation, the image quality is drastically impaired under certain circumstances. For greater comfort, efforts have been made to make the angle as great as possible in order that the display can be tilted from the viewing direction of an observer without significant reduction of the image quality. More recently, for the improvement of viewing angle dependence, experiments have been undertaken to employ liquid crystalline compounds whose dipole moment perpendicular to the molecular longitudinal axis is greater than parallel to the longitudinal axis of the molecule. The dielectric anisotropy $\Delta\in$ is negative. In the field-free state, these molecules are orientated perpendicular to the glass surface of the display. By realization of a number of domains, it was possible using liquid crystalline media having negative dielectric anisotropy to achieve an improvement in the viewing angle dependence. Shorter switching times in displays and better contrasts can also be achieved using this technology. Displays of this type are designated as VA-TFT displays (derived from: "vertically aligned").

Development in the field of liquid crystalline materials is by far still not complete. For the improvement of the properties of liquid crystalline display elements, it is constantly being attempted to develop novel compounds which make possible optimization of displays of this type.

B. Zajc and M. Zupan, J. Org. Chem. 1990, 55, 1099-1102, describe the preparation of the following benzo-chroman derivatives:

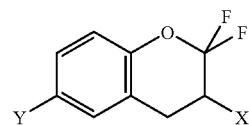

where Y is hydrogen or fluorine and X is hydrogen, fluorine or chlorine. Mesogenic or liquid crystalline properties of these compounds or an appropriate use are not disclosed.

An object of the present invention is therefore to make available compounds having advantageous properties for use in liquid crystalline media. In particular, they should have a negative dielectric anisotropy which makes them particularly suitable for use in liquid crystalline media for VA displays.

This object is achieved according to the invention by compounds of the general formula I

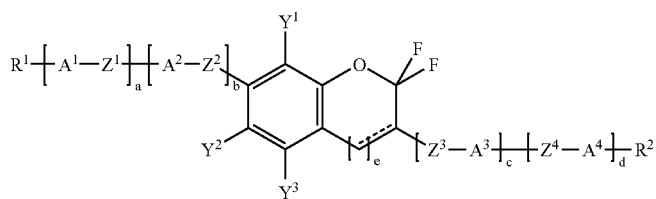

in which:

a, b, c, d and e independently of one another are 0 or 1;

$R^1$ and $R^2$ independently of one another are hydrogen, —F, —Cl, —Br, —I, —CN, —SCN, —NTS, —$SF_5$, an alkanyl, alkoxy, alkenyl or alkynyl having up to 15 carbon atoms, which is unsubstituted, monosubstituted by —CN or —$CF_3$ or monosubstituted or polysubstituted by F, Cl, Br and/or I, where in these radicals one or more $CH_2$ groups can also in each case independently of one another be replaced by —O—, —S—, —$SO_2$—, —CO—, —(CO)O—, —O(CO)— or —O(CO)O—, such that hetero-atoms are not directly linked, or are a polymer-izable group P;

$Y^1$, $Y^2$, and $Y^3$ independently of one another are hydrogen, halogen, halogenated alkyl or halogenated alkoxy having 1 to 8 carbon atoms;

$A^1$, $A^2$, $A^3$ and $A^4$ independently of one another are 1,4-phenylene which can be unsubstituted or mono- to tetra-substituted independently of one another by —CN, —F, —Cl, —Br, —I, $C_1$-$C_6$-alkanyl which can be unsubstituted or mono- or poly-substituted by fluorine and/or chlorine, $C_1$-$C_6$-alkoxy which can be unsubstituted or mono- or poly-substituted by fluorine and/or chlorine; 1,4-cyclohexylene, 1,4-cyclohexenylene or 1,4-cyclohexadi-enylene, in which —$CH_2$— can independently of one another be replaced once or twice by —O— or —S— such that heteroatoms are not directly linked, and which can be unsubstituted or mono- or polysubstituted by —F, —Cl, —Br and/or —I;

$Z^1$, $Z^2$, $Z^3$ and $Z^4$ independently of one another are a single bond, —$CF_2$O—, —$OCF_2$—, —$CH_2CH_2$—, —$CF_2CF_2$—, —$CF_2CH_2$—, —$CH_2CF_2$—, —CHF—CHF—, —(CO)O—, —O(CO)—, —$CH_2$O—, —$OCH_2$—, —CF=CH—, —CH=CF—, —CF=CF—, —CH=CH— or —C≡C—; and ⚟ in the oxygen heterocycle of the formula I is a C—C single bond and, if e is 1, can also be a C=C double bond;

where $Y^2$ is not hydrogen or fluorine and $R^2$ is not hydrogen, fluorine or chlorine if at the same time a, b, c and d are 0 and e is 1 and $R^1$ is hydrogen and $Y^1$ and $Y^3$ are both hydrogen and ⚟ is a single bond.

The compounds preferably have a negative $\Delta\epsilon$ and are therefore particularly suitable for use in VA-TFT displays. Preferably, the compounds according to the invention have a $\Delta\epsilon$<−2 and particularly preferably a $\Delta\epsilon$<−5. They show very good compatibility with the customary substances used in liquid crystal mixtures for displays.

Furthermore, the compounds of the formula I according to the invention have suitable values of the optical anisotropy $\Delta n$, in particular for use in VA-TFT displays. Preferably, the compounds according to the invention have a $\Delta n$ of greater than 0.02 and less than 0.40, preferably of greater than 0.04 and less than 0.15.

The further physical, physicochemical or electro-optical parameters of the compounds according to the invention are also advantageous for use of the compounds in liquid crystalline media. The compounds in particular have an adequate breadth of the nematic phase and a good low-temperature and long-term stability and also adequately high clear points.

The compounds of the formula I according to the invention are furthermore suitable for the preparation of further, optionally more complex mesogenic or liquid crystalline substances which possess a structural element having a benzo-fused and difluoro-substituted oxygen heterocycle.

The compounds of the formula I according to the invention are benzochroman derivatives, i.e. e=1 and ⚟ is a C—C single bond, benzochromene derivatives, i.e. e=1 and ⚟ is a C—C double bond, or benzofuran derivatives, i.e. e=0 and ⚟ is a C—C single bond which is linked directly to the aromatic ring. Benzochroman and benzochromene derivatives are preferred here, i.e. e is preferably 1. Benzochroman derivatives of the formula I are particularly preferred, i.e. e is 1 and ⚟ is a C—C single bond.

If $R^1$ and $R^2$ in formula I in each case independently of one another are an alkanyl radical and/or an alkoxy radical (alkyloxy radical) having 1 to 15 C atoms, these are straight-chain or branched. Preferably, each of these radicals is straight-chain, has 1, 2, 3, 4, 5, 6 or 7 C atoms and accordingly is preferably methyl, ethyl, propyl, butyl, pentyl, hexyl, heptyl, methoxy, ethoxy, propoxy, butoxy, pentoxy, hexoxy or heptoxy.

$R^1$ and $R^2$ in formula I can in each case independently of one another also be an oxaalkyl radical, i.e. an alkanyl radical, in which at least one of the nonterminal $CH_2$ groups of the alkanyl radical is replaced by —O—, preferably straight-chain 2-oxapropyl (=methoxymethyl), 2-(=ethoxymethyl) or 3-oxabutyl (=methoxyethyl), 2-, 3- or 4-oxapentyl, 2-, 3-, 4- or 5-oxahexyl, 2-, 3-, 4-, 5- or 6-oxaheptyl. Correspondingly, $R^1$ and $R^2$ in formula I can also independently of one another be thioalkanyl or sulfonalkanyl radicals, i.e. alkanyl radicals in which a $CH_2$ group is replaced by —S— or —$SO_2$—.

$R^1$ and $R^2$ in formula I can furthermore in each case independently of one another be an alkenyl radical having 2 to 15 C atoms, which is straight-chain or branched and has at least one C—C double bond. Preferably, it is straight-chain and has 2 to 7 C atoms. Accordingly, it is preferably vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl. If the two C atoms of the C—C double bond are substituted, the alkenyl radical can be present as an E and/or Z isomer (trans/cis). In general, the respective E isomers are preferred.

In the same manner as in the case of an alkanyl radical, at least one of the CH$_2$ groups in an alkenyl radical can be replaced by oxygen, sulfur or —SO$_2$—. In the case of replacement by —O—, an alkenyloxy radical (having a terminal oxygen) or an oxaalkenyl radical (having a nonterminal oxygen) is then present.

R$^1$ and R$^2$ in formula I can independently of one another also be an alkynyl radical having 2 to 15 C atoms, which is straight-chain or branched and has at least one C—C triple bond.

R$^1$ and R$^2$ in formula I can in each case independently of one another be an alkanyl radical having 1 to 15 C atoms, in which one CH$_2$ group is replaced by —O— and one by —CO—, where these are preferably adjacent. This thus comprises an acyloxy group —CO—O— or an oxy-carbonyl group —O—CO—. Preferably, this radical is straight-chain and has 2 to 6 C atoms. The following of these radicals are preferred here: acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxy-ethyl, 2-butyryloxyethyl, 2-acetyloxypropyl, 3-prop-ionyloxypropyl, 4-acetyloxybutyl, methoxycarbonyl, ethoxycarbonyl, propoxycarbonyl, butbxycarbonyl, pentoxycarbonyl, methoxycarbonylmethyl, ethoxycarbonyl-methyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl. Furthermore, an alkanyl radical can also have an —O—CO—O— unit. The replacement of a CH$_2$ group by only one —CO— group (carbonyl function) is also possible.

R$^1$ and R$^2$ in formula I can in each case independently of one another be an alkenyl radical having 2 to 15 C atoms, in which a CH$_2$ group, preferably in the neighborhood of an unsubstituted or substituted —C=C— unit, is replaced by —CO—, —CO—O—, —O—CO— or —O—CO—O—, where this radical can be straight-chain or branched. Preferably, the radical is straight-chain and has 4 to 13 C atoms. Acryloyloxymethyl, 2-acryloyloxyethyl, 3-acryloyloxypropyl, 4-acryloyloxybutyl, 5-acryloyloxy-pentyl, 6-acryloyloxyhexyl, 7-acryloyloxyheptyl, 8-acryloyloxyoctyl, 9-acryloyloxynonyl, methacryloyl-oxymethyl, 2-methacryloyloxyethyl, 3-methacryloyloxy-propyl, 4-methacryloyloxybutyl, 5-methacryloyloxy-pentyl, 6-methacryloyloxyhexyl, 7-methacryloyloxyheptyl or 8-methacryloyloxyoctyl are particularly preferred here. Correspondingly, a CH$_2$ group in an alkynyl radical, in particular in the neighborhood of a substituted —C≡C— unit, can also be replaced by —CO—, —CO—O—, —O—CO— or —O—CO—O—.

R$^1$ and R$^2$ in formula I can in each case independently of one another be an alkanyl radical in which two or more CH$_2$ groups can be replaced by —O— and/or —CO—O—, where these can be straight-chain or branched. Preferably, it is branched and has 3 to 12 C atoms.

R$^1$ and R$^2$ in formula I can in each case independently of one another be an alkanyl radical or alkoxy radical having 1 to 15 C atoms, which is monosubstituted by —CN or —CF$_3$ or a correspondingly substituted alkenyl radical or alkynyl radical having 2 to 15 C atoms, where these are preferably straight-chain. The substitution by —CN or —CF$_3$ is possible in any desired position.

R$^1$ and R$^2$ in formula I can in each case independently of one another be an alkanyl radical or alkoxy radical having 1 to 15 C atoms, which is monosubstituted or polysubstituted by F, Cl, Br and/or I, or an alkenyl radical, alkenyloxy radical or alkynyl radical having 2 to 15 C atoms, where these radicals are preferably straight-chain and halogen is preferably —F and/or —Cl. In the case of polysubstitution halogen is preferably —F. The resulting radicals also include perfluorinated radicals such as —CF$_3$. The mono- or polyfluorinated radicals are also termed "fluoroalkyl", "fluoroalkanyl", "fluoroalkoxy", "fluoroalkenyl", "fluoroalkenyloxy" and "fluoroalkynyl". In the case of monosubstitution the fluorine or chlorine substituent can be in any desired position, preferably in the ω-position.

R$^1$ and R$^2$ in formula I can also in each case independently of one another be —F, —Cl, —Br, —I, —CN, —SCN, —NCS OR —SF$_5$.

R$^1$ and R$^2$ in formula I can also independently of one another be a polymerizable or reactive group P; this is distinguished in that it is able to react in a polymerization reaction, e.g. a free radical or ionic chain polymerization, or in a polyaddition or polycondensation, or in that it can be grafted onto a polymer backbone in a manner analogous to a polymerization reaction, for example by condensation or addition. Particularly preferred groups P are those for chain polymerization reactions such as free radical, anionic or cationic polymerization. Very particularly preferred polymerizable groups P are those which comprise a C—C double bond or a C—C triple bond or which can polymerize with ring opening, e.g. oxetanes or epoxides.

These very particularly preferred polymerizable groups P are selected from the group PI, which comprises:

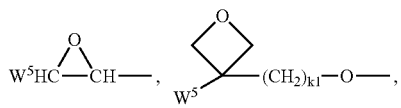

CH$_2$=CW$^5$—(O)$_{k1}$—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N, (CH$_2$=CH—CH$_2$)$_2$N—CO—, HO—CW$^5$W$^6$—, HS—CW$^5$W$^6$—, HW$^5$N—, HO—CW$^5$W$^6$—NH—, CH$_2$=CW$^4$—CO—NH—, CH$_2$=CH—(COO)$_{k1}$-Phe-(O)$_{k2}$—, Phe-CH=CH—, HOOC—, OCN— and W$^7$W$^8$W$^9$Si—, where W$^4$ is H, Cl, CN, phenyl or alkyl having 1 to 5 carbon atoms, in particular H, Cl or CH$_3$, W$^5$ and W$^6$ independently of one another are H or alkyl having 1 to 5 carbon atoms, in particular methyl, ethyl or n-propyl, W$^7$, W$^8$ and W$^9$ independently of one another are Cl, oxaalkyl or oxacarbonylalkyl having 1 to 5 carbon atoms, Phe is 1,4-phenylene which can optionally be monosubstituted or polysubstituted by halogen, and k$_1$ and k$_2$ independently of one another are 0 or 1.

Among these groups P', CH$_2$=CH—COO—, CH$_2$=C(CH$_3$)—COO—, CH$_2$=CCH—, CH$_2$=CH—O—, (CH$_2$=CH)$_2$CH—OCO—, (CH$_2$=CH)$_2$CH—O— and

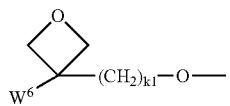

are extremely preferred, where a vinyl group, an acrylate group, a methacrylate group, an oxetane group or an epoxy group, especially an acrylate or methacrylate group, may expressly be mentioned. Acrylate and oxetane groups are particularly preferred.

The polymerizable group P or P' can also contain one of the suitable spacers known in the prior art between the actual reactive polymerizable group and the radical or the ring to which the group P or P' is linked, inter alia ethylene, propylene or butylene. The polymerizable group P is then, for example, a group P'-spacer-, where P' is one of the abovementioned polymerizable functional radicals P' and "spacer" is one of the spacers known in the prior art.

Preferably, $R^1$ and $R^2$ independently of one another are alkanyl, alkenyl or alkoxy, in each case having up to 8 carbon atoms, hydrogen, fluorine or chlorine, particularly preferably alkanyl, alkoxy, fluorine or hydrogen. In particular, $R^1$ is alkoxy or fluorine and $R^2$ is alkanyl.

$Y^1$, $Y^2$ and $Y^3$ are preferably independently of one another fluoroalkanyl, fluoroalkenyl, fluoroalkenyloxy or fluoroalkoxy, in each case having up to 4 carbon atoms, hydrogen, fluorine or chlorine. Particularly preferably, $Y^2$ and $Y^3$ are in each case hydrogen and $Y^1$ is hydrogen, F, $C_1$ or $CF_3$. Very particularly preferably, $Y^2$ and $Y^3$ are hydrogen and $Y^1$ is hydrogen or fluorine, in particular fluorine.

The rings $A^1$, $A^2$, $A^3$ and 4 are preferably selected independently of one another from the group which comprises

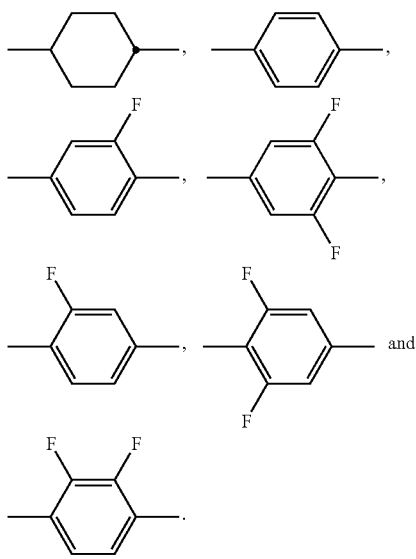

Among the phenylene rings,

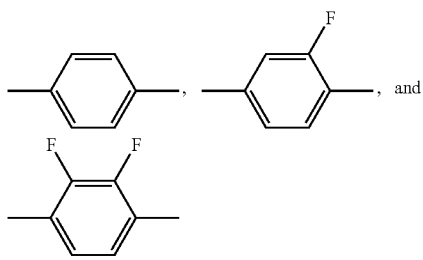

are preferred here.

$Z^1$, $Z^2$, $Z^3$ and $Z^4$ are independently of one another preferably a single bond, —CF$_2$O—, —OCF$_2$—, —CH$_2$CH$_2$—, —CF$_2$CF$_2$— or —CH=CH—, particularly preferably a single bond, —CF$_2$O— or —OCF$_2$—, in particular a single bond.

In addition to the central benzo-fused oxygen heterocycle, the compounds of the formula I according to the invention either have one further or two further ring systems of the formulae $A^1$, $A^2$, $A^3$ and/or $A^4$, i.e. a+b+c+d is preferably 1 or 2. If only one further ring is present, i.e. a+b+c+d=1, it can either be present on the "left" side of the molecule of the formula I, i.e. be linked with the central aromatic ring, or on the "right" side of the molecule of the formula I, i.e. be linked with the central heterocycle. The one ring is preferably linked to the central heterocycle. If two further rings are present, they can both be present on the "left" side of the molecule of the formula I or both be present on the "right" side of the molecule of the formula I, or one of the two radicals is linked to the central aromatic ring, while the other is linked to the central O heterocycle. Here, "be linked" means that the respective ring is bonded to the central ring system either directly via a single bond or indirectly via a bridge Z, which is not a single bond. Particularly preferably, only one further ring is present or, in the case that two further rings are present, in each case one of the rings is linked to the central aromatic ring or to the central heterocycle.

A preferred embodiment of the invention are benzo-chroman derivatives of the formula I, in which a and d are both 0; b is 0 or 1, c is 1; $R^1$, if b is 0, is alkanyl or alkoxy, and if b is 1, is F, alkanyl or alkoxy; $R^2$ is alkanyl or alkoxy; $A^2$, if b is 1, is

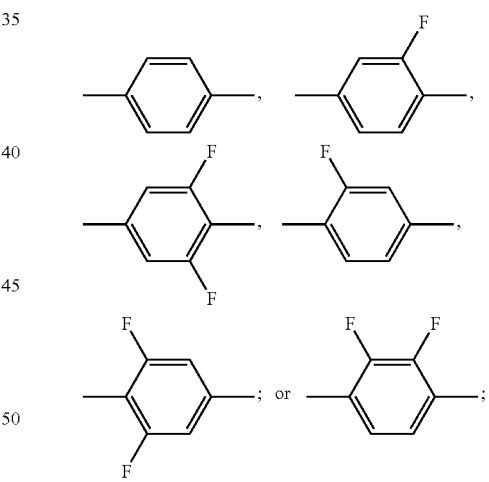

$A^3$ is

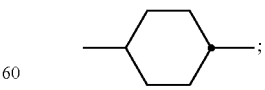

$Z^2$, if b is 1, is a single bond; and $Z^3$ is a single bond.

Preferred benzochroman derivatives of the formula I according to the invention, in which a+b+c+d is 0, are shown by the general formula IA:

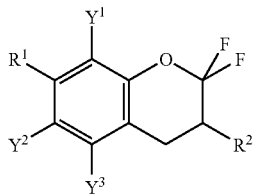
IA where $R^1$, $R^2$, $Y^1$, $Y^2$ and $Y^3$ have the same meanings and the same preferred meanings as defined above for formula I.

Preferred benzochroman derivatives of the formula I according to the invention, in which a+b+c+d is 1, are shown by the general formulae IB and IC:

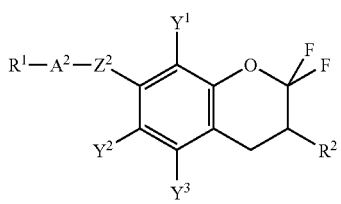
IB

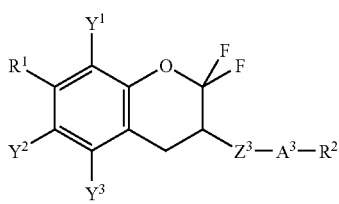
IC where $R^1$, $R^2$, $A^2$, $A^3$, $Z^2$, $Z^3$, $Y^1$, $Y^2$ and $Y^3$ have the same meanings and the same preferred meanings as defined above for formula I.

Preferred benzochroman derivatives of the formula I according to the invention, in which a+b+c+d is 2, are shown by the general formulae ID, IE and IF:

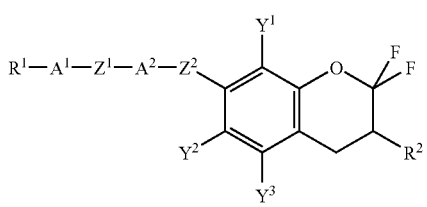
ID

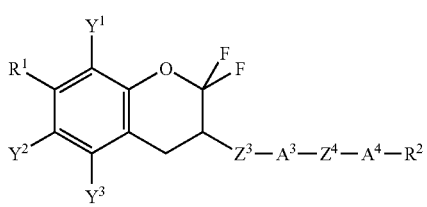
IE

-continued

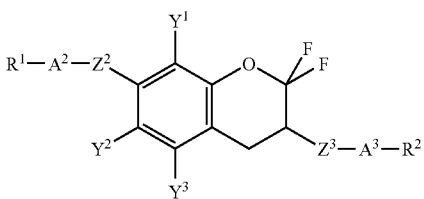
IF where, $R^1$, $R^2$, $A^1$, $A^2$, $A^3$, $Z^1$, $Z^2$, $Z^3$, $Z^4$, $Y^1$, $Y^2$ and $Y^3$ have the same meanings and the same preferred meanings as defined above for formula I.

Among the compounds of the formulae IA to IF according to the invention, compounds of the formulae IB, IC and IF are particularly preferred, especially compounds of the formulae IC and IF.

Exemplary compounds of the formula IB are the following compounds:

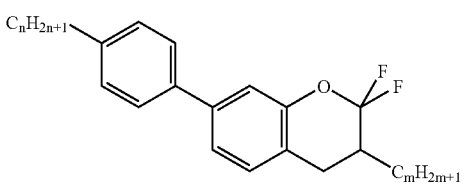
IB-a

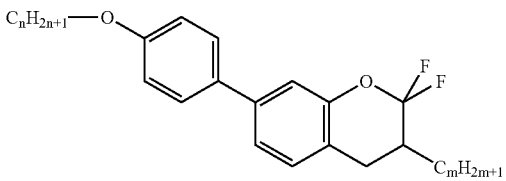
IB-b

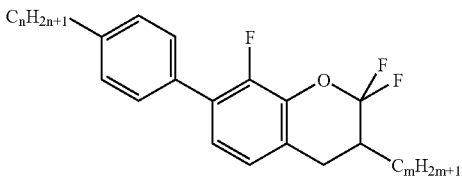
IB-c

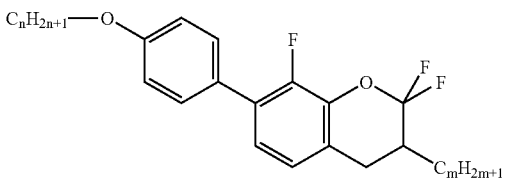
IB-d where n and m independently of one another are 1, 2, 3, 4, 5, 6, 7 or 8, where in the formulae IB-a and IB-c n can also be 0 and in all formulae IB-a to IB-D m can also be 0.

Exemplary compounds of the formula IC are the following compounds:

IC-a

IC-b

IC-c

IC-d

IC-e

IC-f where n and m independently of one another are 1, 2, 3, 4, 5, 6, 7 or 8, where in the formulae IC-a, IC-b, IC-c and IC-e, n can also be 0 and in all formulae IC-a to IC-f, m can also be 0.

Exemplary compounds of the formula IF are the following compounds:

IF-a

IF-b

IF-c

IF-d

IF-e

IF-f

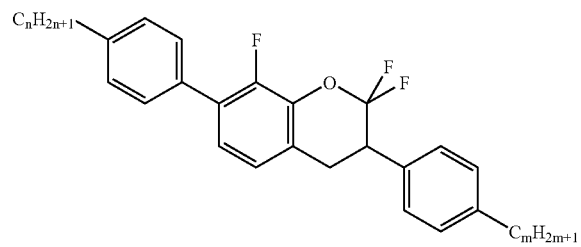

IF-g

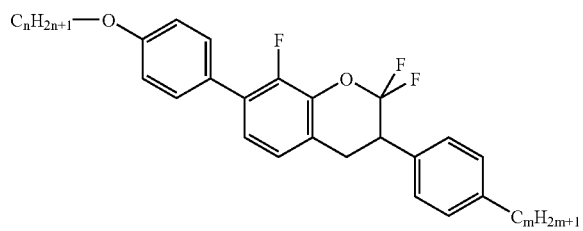

IF-h

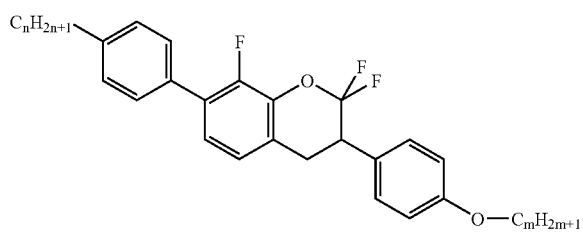

IF-i

[structure]

IF-j

[structure]

where n and m independently of one another are 1, 2, 3, 4, 5, 6, 7 or 8, where in the formulae IF-a, IF-c, IF-e, IF-f, IF-h and IF-j, n can also be 0 and in the formulae IF-a, IF-b, IF-e, IF-f, IF-g and IF-j, m can also be 0.

The compounds of the general formula I are prepared by methods known per se, as are described in the literature (e.g. in the standard works such as Houben-Weyl, Methoden der organischen Chemie [Methods of organic chemistry], Georg-Thieme-Verlag, Stuttgart), namely under reaction conditions which are known and suitable for the reactions mentioned. Use can be made here of variants which are known per se, but not mentioned here in more detail. The starting substances can optionally also be formed in situ in such a way that they are not isolated from the reaction mixture, but immediately reacted further to give the compounds of the general formula I. The starting substances can be obtained according to generally accessible literature procedures or are commercially available.

The compounds of the formula I according to the invention, however, are also accessible according to a process which is a further subject of the present invention. The process according to the invention is characterized in that a compound of the general formula II:

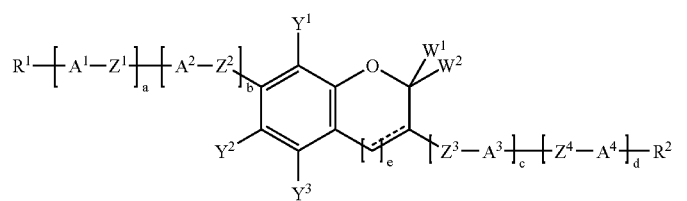

II in which
a, b, c, d, e, $R^1$, $R^2$, $A^1$, $A^2$, $A^3$, $A^4$, $Y^1$, $Y^2$, $Y^3$, $Z^1$, $Z^2$, $Z^3$, $Z^4$ and ⚍ are as defined for formula I and preferably have the same preferred meanings as for formula I;
$W^1$ is —$SR^3$ and
$W^2$ is —$SR^4$;
or
$W^1$ and $W^2$ together are =S or —S—$W^3$—S—,
where
$R^3$ and $R^4$ independently of one another is alkyl having 1 to 8 carbon atoms; and
$W^3$ is a bivalent organic radical having at least two carbon atoms;

is reacted with a fluoride-releasing compound in the presence of an oxidant.

Here, the fluoride-releasing compound is preferably selected from the group which comprises HF, pyridine-hydrogen fluoride complexes, triethylamine trishydro-fluoride ($Et_3N.3HF$) and tetrabutylammonium dihydrogen-trifluoride. Pyridine-hydrogen fluoride complexes and triethylamine trishydrofluoride, in particular triethylamine trishydrofluoride, are particularly preferred.

The oxidant is preferably selected from the group which comprises dimethyldibromohydantoin (DBH), N-chlorosuccinimide (NCS), N-bromosuccinimide (NBS), N-iodosuccinimide (NIS), chlorine, bromine, $SO_2Cl_2$, $SO_2ClF$, $NOBF_4$ and chloramine T. The oxidant dimethyldibromohydantoin, N-bromosuccinimide or bromine, in particular DBH, is particularly preferred.

The exact choice of the reaction conditions of the process according to the invention is not critical per se, provided the reaction of the compound of the formula II to give the compound of the formula I according to the invention proceeds rapidly enough and with adequate selectivity without undesired reaction of reactants, products and reagents. These reaction conditions follow from those of analogous oxidative fluorodesulturization reactions for the introduction of —$CF_2O$— bridges into open-chain compounds, such as are described, inter alia, in P. Kirsch et al, Angew. Chem. 2001, 113, 1528-1532; WO 01/64667 A1, WO 02/48073 A1 and WO 03/033619 A1.

The fluoride-releasing compound is customarily employed in an amount such that—based on the compound of the formula II to be fluorinated approximately 2 to approximately 50 mol equivalents, preferably approximately 5 to approximately 25 mol equivalents and particularly preferably approximately 10 to approximately 20 mol equivalents of fluoride ions are released. If, for example, triethylamine trishydro-fluoride is used as the fluoride-releasing compound, which releases 3 equivalents of fluoride from 1 equivalent of the compound, this reagent is employed in an amount from approximately 0.65 to approximately 16.7 mol equivalents of the compound, based on the compound of the formula II to be reacted, preferably in an amount from approximately 1.65 to approximately 8.4 mol equivalents and particularly preferably in an amount from approximately 3.3 to approximately 6.6 mol equivalents. The oxidant is customarily used in an amount from approximately 2 to approximately 10 mol equivalents—based on the compound of the formula II to be reacted—, particularly preferably in an amount from approximately 3 to approximately 7 mol equivalents and in particular in an amount from approximately 4.5 to approximately 5.5 mol equivalents.

The process according to the invention can be carried out solvent-free and is preferably carried out in a solvent or a mixture of one, two, three or more solvents which is adequately inert to reactants, products and reagents. Preferably, these are polar solvents or solvent mixtures such as ethers, e.g. diethyl ether, methyl tert-butyl ether and tetrahydrofuran (THF) and haloalkanes, e.g. dichloro-methane, trichloromethane and trichloroethylene. Particularly preferably, an individual solvent is used, in particular dichloromethane.

The process according to the invention is carried out in a temperature range from approximately −100° C. to approximately 50° C., depending on the reaction rate, selectivity and exothermicity of the reaction.

The reaction period is likewise especially determined by the rate at which the reaction according to the invention proceeds, and is customarily between 10 min and 2 days, preferably between 1 hour and 24 hours and in particular between 2 hours and 6 hours.

The compounds of the formula II defined above employed in the process according to the invention for the preparation of the compounds of the formula I according to the invention are for their part novel and a further subject of the present invention; here, the radicals, substituents and parameters a, b, c, d, e, $R^1$, $R^2$, $A^1$, $A^2$, $A^3$, $A^4$, $Y^1$, $Y^2$, $Y^3$, $Z^1$, $Z^2$, $Z^3$, $Z^4$ and ⚍ assume the same meanings and preferably the same preferred meanings as for formula I. Excluded from this is the compound of the formula II, in which a, b, c and d simultaneously are all 0 and e is 1 and $R^1$ and $R^2$ are both hydrogen and $Y^1$, $Y^2$ and $Y^3$ are all hydrogen and ⚍ is a C—C single bond and $W^1$ and $W^2$ are together —S—$W^3$—S— where $W^3$ is equal to —$CH_2$—$CH_2$— (E. J. Corey, D. J. Beamers, J. Am. Chem. Soc. 1973, 95, 5829-5831). This compound is only excluded as such, but is employed according to the invention in the process according to the invention for the preparation of the corresponding compound of the formula I.

If $W^1$ is —S—$R^3$ and $W^2$ is —S—$R^4$, $R^3$ and $R^4$ independently of one another are preferably alkanyl radicals having 1, 2, 3, 4, 5 or 6 carbon atoms, in particular methyl, ethyl, n-propyl, i-propyl and n-butyl. $R^3$ and $R^4$ can be identical or different and are preferably identical.

If $W^1$ and $W^2$ together are —S—$W^3$—S—, the bivalent organic radical $W^3$ having at least two carbon atoms is preferably an alkylene bridge having 2, 3, 4, 5 or 6 carbon atoms in the bridge, where up to three of these carbon atoms in each case can have one or two further $C_1$-$C_4$-alkanyl substituents; it is also possible that two adjacent carbon atoms of the alkylene bridge for their part are part of a further ring or ring system, such as, for example, in

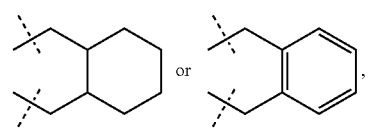

Furthermore, W is preferably a benzene ring which can optionally have further substituents. Particularly preferably, $W^3$ is ethylene (—$CH_2$—$CH_2$—) or propylene (—$CH_2$—$CH_2$—$CH_2$—).

The compounds of the formula II according to the invention are for their part accessible in various ways from substances which are known from the literature or commercially obtainable. In a preferred embodiment, which is also a preferred embodiment of the process according to the invention for preparation of compounds of the formula I, the compound of the formula II is obtained from a lactone of the general formula III by reaction with a reagent which is obtainable by reaction of approximately 2 mol equivalents of trialkylaluminum with approximately 1 mol equivalent of HS—$W^3$—SH and is preferably formed in situ. Here, the lactone has the following formula III

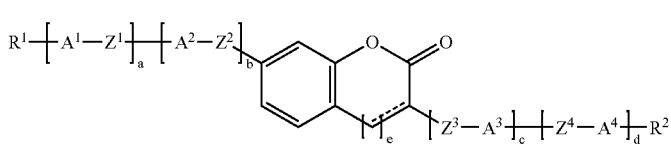

III in which a, b, c, d, e, $R^1$, $R^2$, $A^1$, $A^2$, $A^3$, $A^4$, $Z^1$, $Z^2$, $Z^3$, $Z^4$ and ⌀ are as defined for the formulae I and II.

Preferably, the trialkylaluminum employed is a trimethylaluminum. $W^3$ in the dithiol HS—$W^3$—SH has the same meaning and the same preferred meaning as in formula II.

The lactone of the formula III can be prepared, for example, as in or analogously to the following scheme 1:

Scheme 1

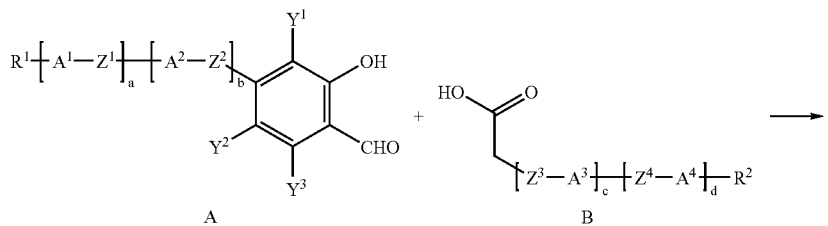

A        B

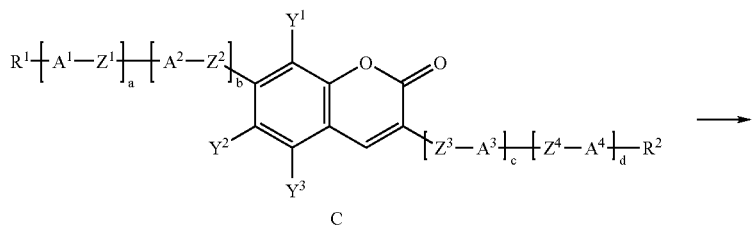

C

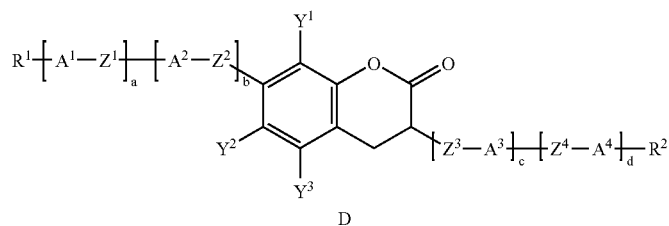

D

Here, the salicylaldehyde A condenses with acetic acid derivatives B to give the lactone C, which can now be employed for its part in the process according to the invention. Alternatively, the endocyclic double bond of C can be reduced under catalytic hydrogenation and the lactone D thus obtained.

A further process for the preparation of lactones employed according to the invention is shown in scheme 2:

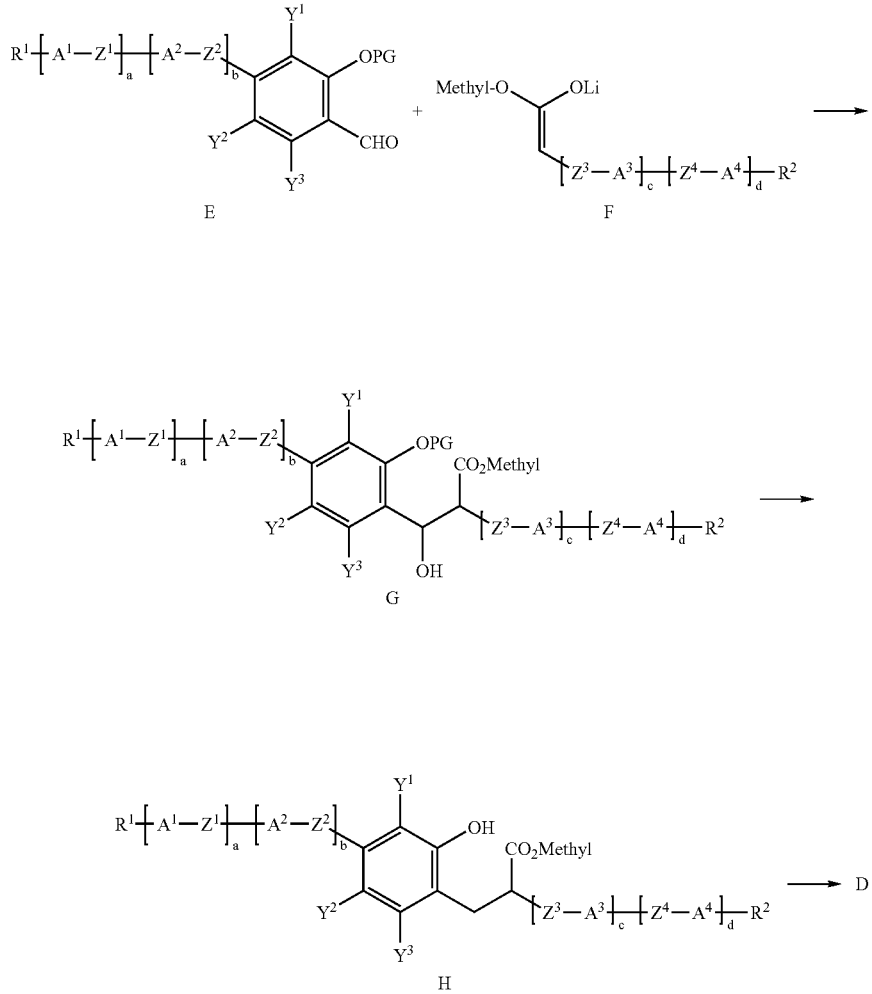

PG = protective group

Here, the salicylaldehyde E is reacted with lithium ester enolates F to give G; by addition of acid, the OH group is eliminated with formation of a C—C double bond, which is subsequently catalytically hydrogenated. The resulting compound H is subsequently converted to the lactone D with acid in methanol or by heating.

A further synthesis (scheme 3) is especially suitable for the preparation of lactones of the formula III, in which c and d are both 0 and $R^2$ is an alkyl radical:

Scheme 3

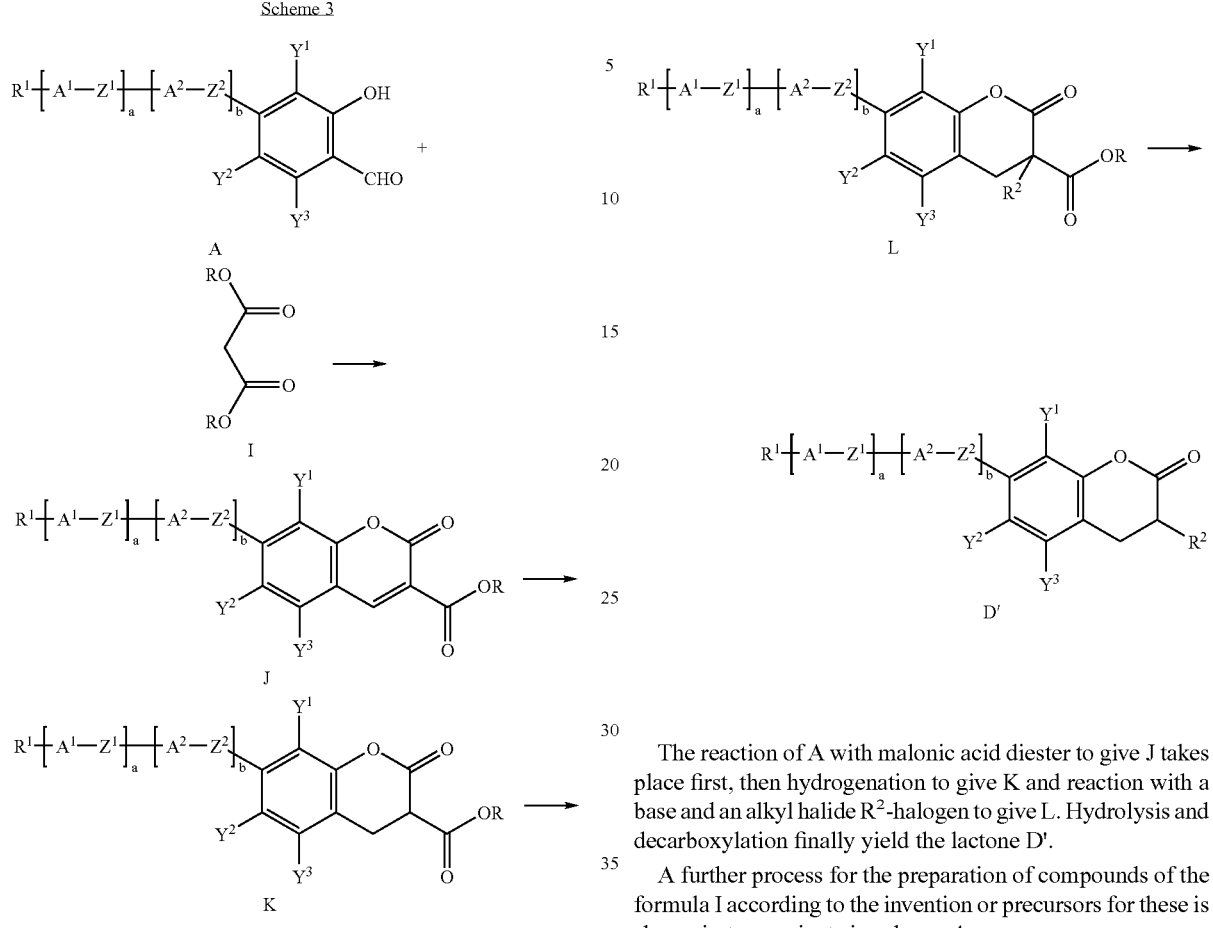

The reaction of A with malonic acid diester to give J takes place first, then hydrogenation to give K and reaction with a base and an alkyl halide $R^2$-halogen to give L. Hydrolysis and decarboxylation finally yield the lactone D'.

A further process for the preparation of compounds of the formula I according to the invention or precursors for these is shown in two variants in scheme 4:

Scheme 4 a)

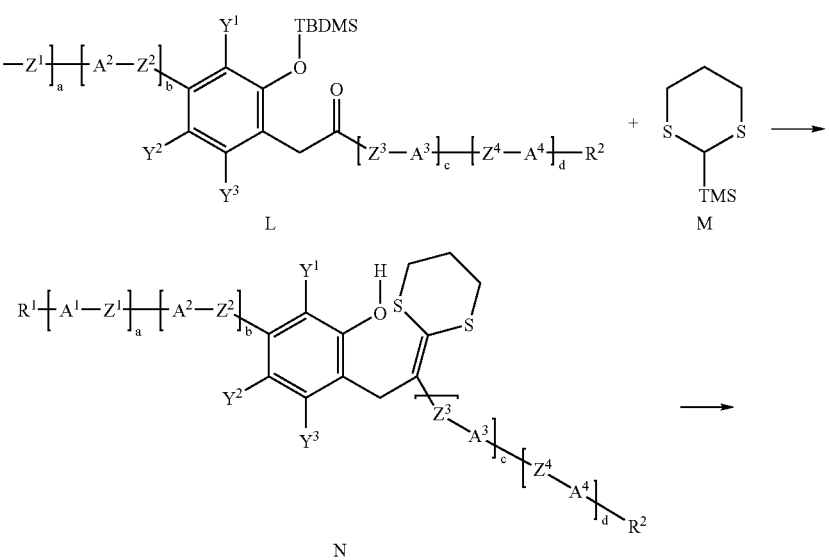

-continued

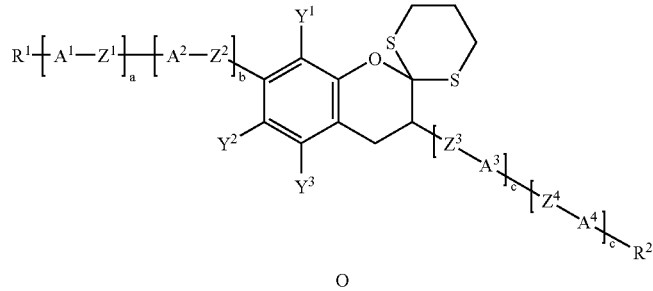

TBDMS = tert-butyldimethylsilyl
TMS = trimethylsilyl b)

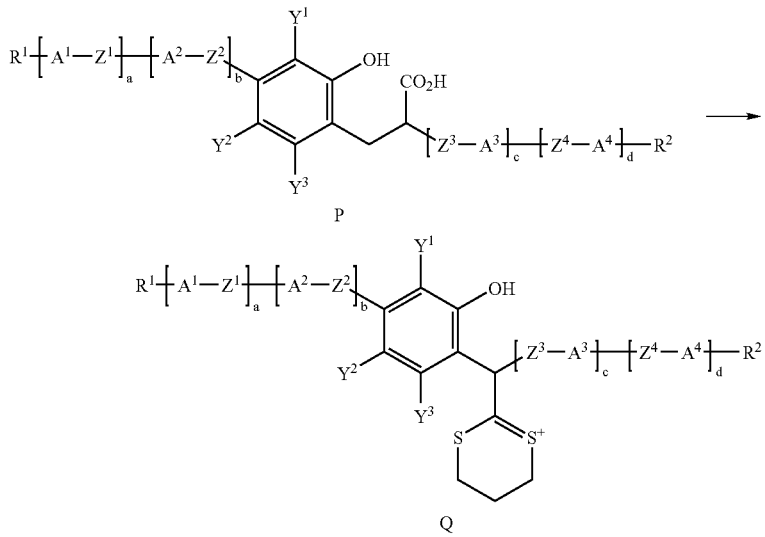

In variant a), the ketone L is converted using the 2-trimethylsilyl-1,3-dithiane M and n-butyllithium and subsequent reaction with tetrabutylammonium fluoride into the ketene dithioketal which for its part is cyclized under acid catalysis to give the spiro compound O, which is a compound of the formula II. In variant b), the carboxylic acid derivative P is activated using thionyl chloride and then reacted with propane-1,3-dithiol in the presence of trifluoroacetic acid to give the salt Q, which for its part can be reacted with a fluoride-releasing compound and an oxidant to give the desired compound of the formula I.

Modifications and variations of the processes mentioned can be performed and carried out without problems by the person skilled in the act on the basis of his knowledge. The study of the attached examples will further illustrate these processes.

As already mentioned, the compounds of the general formula I can be used in liquid crystalline media.

The present invention therefore also relates to a liquid crystalline medium having at least two liquid crystalline compounds, comprising at least one compound of the general formula I, where according to the invention the benzochroman derivatives of the formula I with a, b, c, d equal to 0, $R^1$, $Y^1$ and $Y^3$ equal to hydrogen and $Y^2$ equal to hydrogen or fluorine and $R^2$ equal to hydrogen, fluorine or chlorine, which are already known as such in the prior art, can be employed here.

The present invention also relates to liquid crystalline media comprising as further constituents, in addition to one or more compounds of the formula I according to the invention, 2 to 40, preferably 4 to 30, components. Particularly preferably, in addition to one or more compounds according to the invention these media contain 7 to 25 components. These further constituents are preferably selected from nematic or nematogenic (monotropic or isotropic) substances, in particular substances from the classes consisting of the azoxybenzenes, benzylideneanilines, biphenyls, terphenyls, 1,3-dioxanes, 2,5-tetrahydropyrans, phenyl or cyclohexyl benzoates, cyclohexanecarboxylic acid phenyl or cyclohexyl esters, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid, and of cyclohexylcyclohexanecarboxylic acid, phenylcyclohexanes, cyclohexyl-biphenyls, phenylcyclohexylcyclohexanes, cyclohexyl-cyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenyl-ethanes, optionally halogenated stilbenes, benzyl phenyl ethers, tolanes and substituted cinnamic acids. The 1,4-phenylene groups in these compounds can also be mono- or polyfluorinated.

The most important compounds suitable as further constituents of media according to the invention can be characterized by the formulae (1), (2), (3), (4) and (5):

R'-L-E-R'' (1)

R'-L-COO-E-R'' (2)

R'-L-OOC-E-R'' (3)

R'-L-CH$_2$CH$_2$-E-R'' (4)

R'-L-CF$_2$O-E-R'' (5)

In the formulae (1), (2), (3), (4) and (5), L and E, which can be identical or different, are in each case independently of one another a bivalent radical from the group formed from -Phe-, -Cyc-, -Phe-Phe-, -Phe-Cyc-, -Cyc-Cyc-, -Pyr-, -Dio-, Thp-, -G-Phe- and -G-Cyc-, and their mirror images, where Phe is 1,4-phenylene unsubstituted or substituted by fluorine, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, Thp is tetrahydropyran-2,5-diyl and G is 2-(trans-1,4-cyclohexyl)ethyl, pyrimidine-2,5-diyl, pyridine-2,5-diyl, 1,3-dioxane-2,5-diyl or tetra-hydropyran-2,5-diyl.

Preferably, one of the radicals L and E is Cyc or Phe. E is preferably Cyc, Phe or Phe-Cyc. Preferably, the media according to the invention contain one or more components selected from the compounds of the formulae (1), (2), (3), (4) and (5), in which L and E are selected from the group consisting of Cyc and Phe and simultaneously one or more components selected from the compounds of the formulae (1), (2), (3), (4) and (5) in which one of the radicals L and E is selected from the group Cyc and Phe and the other radical is selected from the group -Phe-Phe-, -Phe-Cyc-, -Cyc-Cyc-, -G-Phe- and -G-Cyc-, and optionally one or more components selected from the compounds of the formulae (1), (2), (3), (4) and (5) in which the radicals L and E are selected from the group consisting of -Phe-Cyc-, -Cyc-Cyc-, -G-Phe- and -G-Cyc-.

In a smaller subgroup of compounds of the formulae (1), (2), (3), (4) and (5), R' and R'' are in each case independently of one another alkyl, alkenyl, alkoxy, alkoxyalkyl(oxaalkyl) alkenyloxy or alkanoyloxy having up to 8 C atoms. Below, this smaller subgroup is called group A and the compounds are designated by the subformulae (1a), (2a), (3a), (4a) and (5a). In most of these compounds, R' and R'' are different from one another, where one of these radicals is usually alkyl, alkenyl, alkoxy or alkoxyalkyl(oxaalkyl).

In another smaller subgroup of the compounds of the formulae (1), (2), (3), (4) and (5) designated as group B, E is

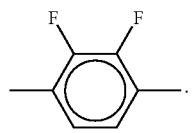

In the compounds of group B, which are designated by the subformulae (1b), (2b), (3b), (4b) and (5b), R' and R'' have the meaning indicated in the case of the compounds of the subformulae (1a) to (5a) and are preferably alkyl, alkenyl, alkoxy or alkoxyalkyl(oxa-alkyl).

In a further smaller subgroup of the compounds of the formulae (1), (2), (3), (4) and (5), R'' is —CN. This subgroup is designated below as group C and the compounds of this subgroup are correspondingly described by subformulae (1c), (2c), (3c), (4c) and (5c) In the compounds of the subformulae (1c), (2c), (3c), (4c) and (5c), R' has the meaning indicated in the case of the subformulae (1a) to (5a) and is preferably alkyl, alkenyl, alkoxy or alkoxyalkyl(oxa-alkyl).

In addition to the preferred compounds of groups A, B and C, other compounds of the formulae (1), (2), (3), (4) and (5) having other variants of the designated substituents are customary. All these substances are obtainable according to methods known in the literature or in analogy thereto.

In addition to the compounds of the general formula I according to the invention, the media according to the invention preferably contain one or more compounds from the groups A, B and/or C. The percentages by weight of the compounds from these groups in the media according to the invention are:

Group A: 0 to 90%, preferably 20 to 90%, in particular 30 to 90%

Group B: 0 to 80%, preferably 10 to 80%, in particular 10 to 70%

Group C: 0 to 80%, preferably 5 to 80%, in particular 5 to 50%.

The media according to the invention preferably contain 1 to 40%, particularly preferably 5 to 30%, of the compounds of the formula I according to the invention. Media comprising more than 40%, in particular 45 to 90%, of compounds of the formula I according to the invention are furthermore preferred. The media preferably contain one, two, three, four or five compounds of the formula I according to the invention.

Examples of the compounds of the formulae (1), (2), (3), (4) and (5) are the compounds listed below:

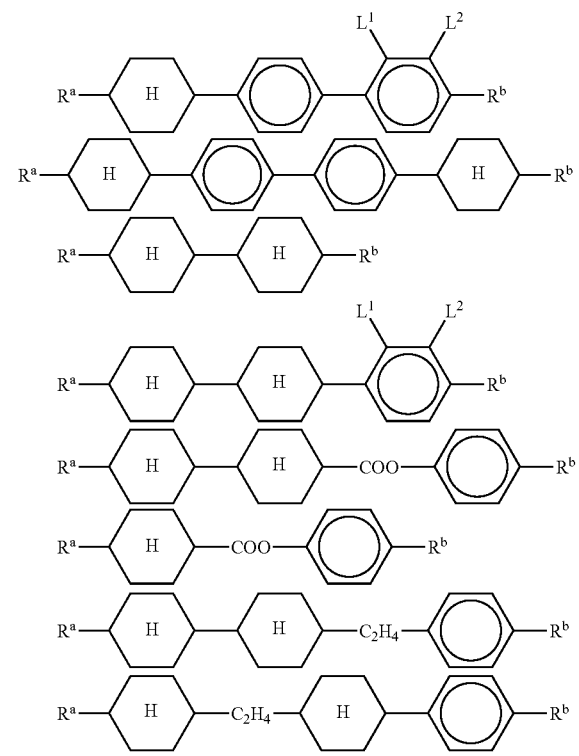

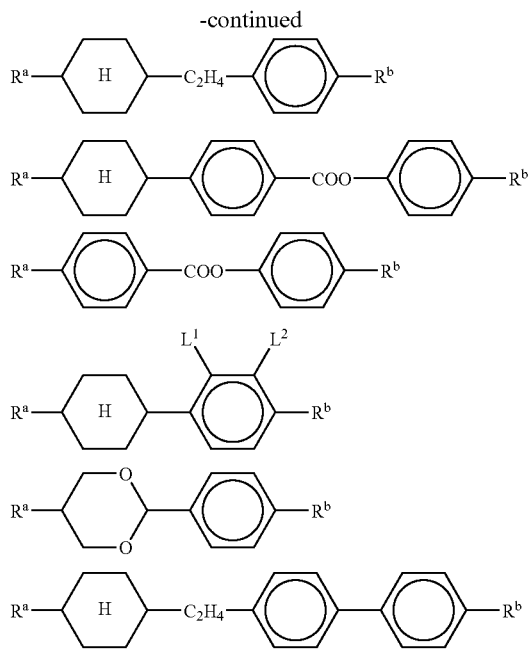
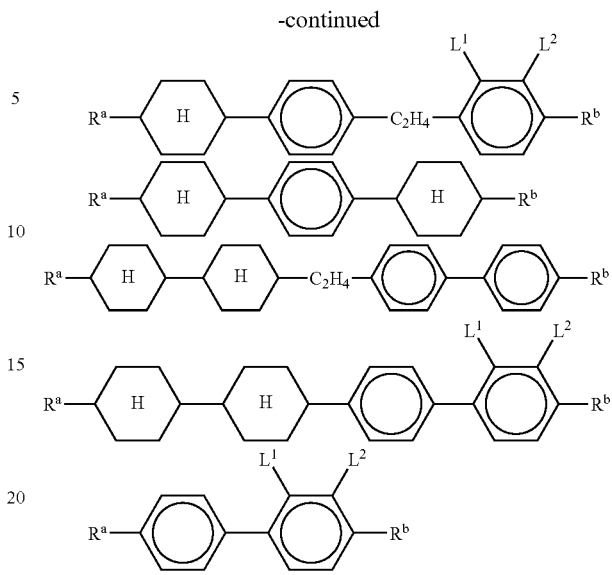
with $R^a$, $R^b$ independently of one another $-C_pH_{2p+1}$ or $-OC_pH_{2p+1}$ and p=1, 2, 3, 4, 5, 6, 7 or 8 and $L^1$, $L^2$ independently of one another —H or —F,
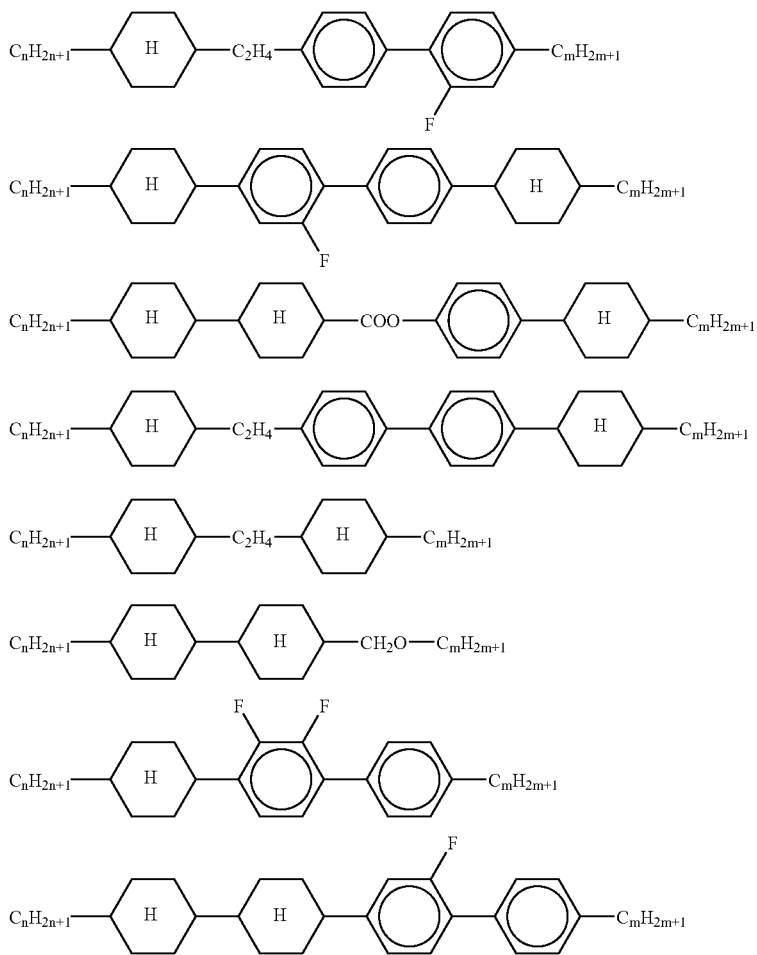

-continued

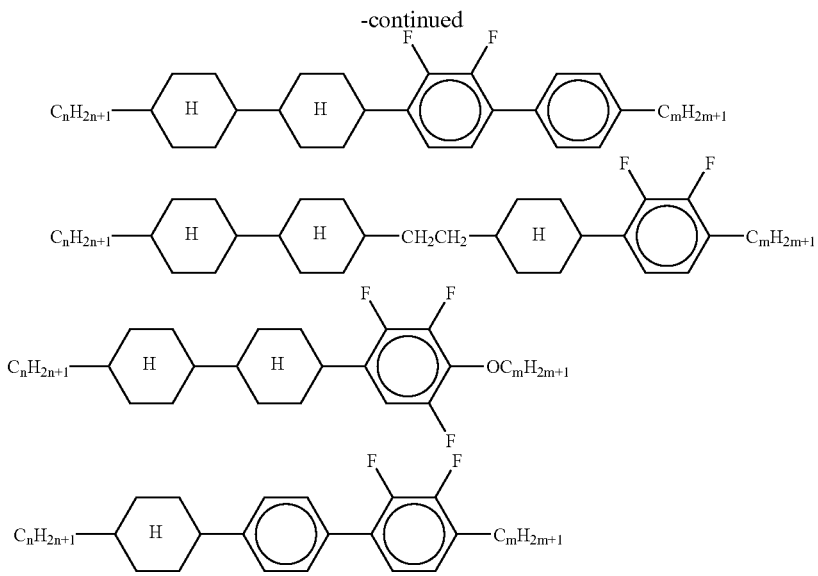

with m, n independently of one another 1, 2, 3, 4, 5, 6, 7 or 8.

The preparation of the media according to the invention is carried out in a manner customary per se. As a rule, the components are dissolved in one another, preferably at elevated temperature. By means of suitable additives, the liquid crystalline phase of the present invention can be modified such that it can be used in all types of liquid crystal display elements which have hitherto become known. Additives of this type are known to the person skilled in the art and described in detail in the literature (H. Kelker/R. Hatz, Handbook Of Liquid Crystals, Verlag Chemie, Weinheim, 1980). For example, pleochroitic dyes can be added for the preparation of colored guest-host systems or substances can be added for the modification of the dielectric anisotropy, the viscosity and/or the orientation of the nematic phases.

Because of their negative $\Delta\epsilon$, the compounds of the formula I are suitable in particular for use in VA-TFT displays.

The present invention therefore also relates to electrooptical liquid crystal display elements comprising a liquid crystalline medium according to the invention.

The invention is explained in more detail below with the aid of exemplary embodiments without, however, being intended to be restricted thereby.

Above and below, $\Delta n$ is the optical anisotropy (589 nm, 20° C.) and $\Delta\epsilon$ is the dielectric anisotropy (1 kHz, 20° C.).

In the context of the present invention, halogen is fluorine, chlorine, bromine and iodine.

In connection with the present invention, the expression "alkyl"—if not defined differently at another place in this description or in the claims—in its most general meaning is a straight-chain or branched, saturated or unsaturated aliphatic hydrocarbon radical having 1 to 15 (i.e. 1, 2, 3, 4, 5, 6, 7, 8, 9, 10, 11, 12, 13, 14 or 15) carbon atoms; this radical is unsubstituted or monosubstituted or polysubstituted by fluorine, chlorine, bromine, iodine, carboxyl, nitro, —NH$_2$, —N(alkanyl)$_2$ and/or cyano, where the polysubstitution can take place by the same or by different substituents. The alkyl radical in the aliphatic hydrocarbon chain itself can also be functionalized.

If this alkyl radical is a saturated radical, it is also designated as "alkanyl". Furthermore, the expression "alkyl" also comprises unsubstituted hydrocarbon radicals or corresponding hydrocarbon radicals which are identically or differently mono- or polysubstituted, in particular by F, Cl, Br, I and/or —CN, in which one or more CH$_2$ groups can be replaced by —O— ("alkoxyl", "oxaalkyl"), —S— ("thioalkyl"), —SO$_2$—, —CH=CH—, ("alkenyl"), C≡C— ("alkynyl"), —CO—, —CO—C— or —O—CO— such that heteroatoms (O,S) in the chain are not linked directly to one another. Preferably, alkyl is a straight-chain or branched unsubstituted or substituted alkanyl, alkenyl or alkoxy radical having 1, 2, 3, 4, 5, 6, 7 or 8 carbon atoms. If alkyl is an alkanyl radical, this is preferably methyl, ethyl, n-propyl, i-propyl, n-butyl, i-butyl, t-butyl, n-pentyl, neopentyl, n-hexyl, n-heptyl, n-octyl; CF$_3$, CHF$_2$, CH$_2$F, CF$_2$CF$_3$. Particularly preferably, the alkanyl radical is straight-chain and unsubstituted or substituted by F.

As in an alkyl radical one or more CH$_2$ groups can be replaced by —O—, the expression "alkyl" also comprises "alkoxy" or "oxaalkyl" radicals. Alkoxy is to be understood as meaning an O-alkyl radical in which the oxygen atom is bonded directly to the group substituted by the alkoxy radical or to the substituted ring and alkyl is defined as above; preferably alkyl is then alkanyl or alkenyl. Preferred alkoxy radicals are methoxy, ethoxy, propoxy, butoxy, pentoxy, hexoxy, heptoxy and octoxy, where each of these radicals can also be substituted, namely preferably by one or more fluorine atoms. Particularly preferably, alkoxy is —OCH$_3$, —OC$_2$H$_5$, —O-n-C$_3$H$_7$, —O-n-C$_4$H$_9$, —O-t-C$_4$H$_9$, —OCF$_3$, —OCHF$_2$, —OCHF or —OCHFCHF$_2$. In connection with the present invention, the expression "oxaalkyl" denotes alkyl radicals in which at least one nonterminal CH$_2$ group is replaced by —O— such that no adjacent heteroatoms (O, S) are present. Preferably, oxaalkyl comprises straight-chain radicals of the formula C$_a$H$_{2a+1}$—O—(CH$_2$)$_b$—, where a and b in each case independently of one another are 1, 2, 3, 4, 5, 6, 7, 8, 9 or 10; particularly preferably, a is an integer from 1 to 6 and b is 1 or 2.

If, in an alkyl radical as defined above, one or more CH$_2$ groups are replaced by sulfur, a "thioalkyl" radical is present. Preferably, "thioalkyl" comprises a straight-chain radical of the formula C$_a$H$_{2a+1}$—S—(CH$_2$)$_b$—, where a is 1, 2, 3, 4, 5, 6, 7, 8, 9 or 10 and b is 0, 1, 2, 3, 4, 5, 6, 7, 8, 9 or 10; particularly preferably, a is an integer from 1 to 6 and b is 0, 1 or 2. The thioalkyl radical can likewise be substituted by F, Cl, Br, I and/or —CN and is preferably unsubstituted.

In the context of the present invention, the expression "alkenyl" is an alkyl radical as defined as above, in which one or more —CH=CH— groups are present. If two —CH=CH— groups are present in the radical, this can also be designated as "alkadienyl". An alkenyl radical can contain 2 to 15 (i.e. 2, 3, 4, 5, 6, 7, 8, 9, 10, 11, 12, 13, 14 or 15) carbon atoms and is branched-chain or preferably straight-chain. The radical is unsubstituted or mono- or polysubstituted identically or differently, in particular by F, Cl, Br, I and/or —CN, i.e. one or both hydrogens of the —CH=CH— unit and/or one or more hydrogens of the further $CH_2$ or $CH_3$ groups of the alkenyl radical can be replaced by the corresponding substituent(s). Furthermore, one or more $CH_2$ groups can in each case independently of one another be substituted by —O—, —S—, —C≡C—, —CO—, —CO—O— or —O—CO— such that heteroatoms (O, S) are not linked directly to one another. Alkenyl radicals in which one $CH_2$ group is replaced by —O— is also designated here as "alkenyloxy". If the CH=CH group carries a radical other than hydrogen on both carbon atoms, for example if it is a nonterminal group, the CH=CH group can be present in two configurations, namely as the E isomer and as the Z isomer. The same applies for the double bond groups substituted by halogen and/or —CN. In general, the E isomer (trans) is preferred. Preferably, the alkenyl radical contains 2, 3, 4, 5, 6 or 7 carbon atoms and is vinyl, allyl, 1E-propenyl, 2-propenyl, 1E-butenyl, 1E-pentenyl, 1E-hexenyl, 1E-heptenyl, 2-propenyl, 2E-butenyl, 2E-pentenyl, 2E-hexenyl, 2E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl and 6-heptenyl, Particularly preferred alkenyl radicals are vinyl, allyl, 1E-propenyl, 2-propenyl and 3E-butenyl.

If, in an alkyl radical, one or more $CH_2$ groups are replaced by —C≡C—, an alkynyl radical is present. The replacement of one or more $CH_2$ groups by —CO—O— or —O—CO— is also possible. The following of these radicals are preferred here: acetyloxy, propionyloxy, butyryl-oxy, pentanoyloxy, hexanoyloxy, acetyloxymethyl, propionyloxymethyl, butyryloxymethyl, pentanoyloxy-methyl, 2-acetyloxyethyl, 2-propionyloxyethyl, 2-butyryloxyethyl, 2-acetyloxypropyl, 3-propionyloxy-propyl, 4-acetyloxybutyl, methoxycarbonyl, ethoxy-carbonyl, propoxycarbonyl, butoxycarbonyl, pentoxy-carbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If, in an alkyl radical, a $CH_2$ group is replaced by unsubstituted or substituted —CH=CH— and an adjacent $CH_2$ group is replaced by CO, CO—C— or O—CO—, this radical can be straight-chain or branched. Preferably, it is straight-chain and has 4 to 12 C atoms. Accordingly, it is particularly preferably acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl or 8-methacryloyloxyoctyl.

If the alkyl radical, alkanyl radical, alkenyl radical or alkoxy radical is substituted by at least one halogen, this radical is preferably straight-chain. Halogen is preferably F or Cl. In the case of poly-substitution, halogen is preferably F. The resulting radicals also include perfluorinated radicals. In the case of monosubstitution, the fluorine or chlorine substituent can be in any desired position, but preferably in the ω position.

In connection with the present invention, the expression "fluoroalkyl" designates an alkyl radical as defined above, which is substituted by one or more fluorine atoms. Preferably, the fluoroalkyl radical has 1 to 7 carbon atoms. Particularly preferred fluoro alkyl radicals are, in addition to $CF_3$ and $CHF_2$, highly fluorinated alkyl radicals such as $C_2F_5$, $CHFCF_3$ and $CHFCHF_2$.

In connection with the present invention, the expression "fluoroalkoxyl" designates an alkoxy radical as defined above, which is substituted by one or more fluorine atoms. Preferably, the fluoroalkoxy radical has 1 to 7 carbon atoms. Particularly preferred fluoro-alkoxy radicals are, in addition to $OCF_3$, $OCHF_2$ and $OCH_2F$, highly fluorinated alkoxy radicals such as $OC_2F_5$, $OCHFCF_3$ and $OCHFCHF_2$.

In the context of the present invention, the expression "aryl"—if it is not defined differently in the individual cases in another position in the description or in the claims—means an aromatic hydrocarbon having 6 to 14 carbon atoms, which is optionally mono- or polysubstituted by halogen, nitro, alkanyl, alkoxy, —$NH_2$ or by —$N(alkanyl)_2$, where the polysubstitution can take place with the same or with different substituents. The expression also comprises aromatic hydrocarbons having more than one ring, i.e. fused ring systems and ring systems having rings linked via single or double bonds. In particular, "aryl" is an unsubstituted or substituted phenyl, naphthyl or 4,4'-biphenyl radical.

In connection with the present invention, the expression "aralkyl" represents an arylalkyl radical, i.e. a radical in which an aryl substituent is linked to an atom, a chain, another radical or a functional group via an alkyl bridge. The alkyl bridge is preferably a saturated bivalent hydrocarbon radical ("alkylene"), in particular methylene (—$CH_2$—) and ethylene (—$CH_2$—$CH_2$—). Preferred examples of an aralkyl radical are benzyl and phenethyl. For the purposes of the present invention, an "aralkyl-O— radical" is an aralkyl radical which is linked to a further atom, a chain, another radical or a functional group via an oxygen atom bonded to the alkyl bridge. Preferred examples of an aralkyl-O— radical are O-benzyl and O—$CH_2CH_2$phenyl.

In the context of the present invention, "alkylenel" or "alkylene bridge"—if the terms are not defined differently in another position in this description or in the claims—represents a bivalent aliphatic hydrocarbon radical having 1, 2, 3, 4, 5, 6, 7, 8 carbon atoms in the chain, which can optionally also be mono- or polysubstituted by halogen, CN, carboxyl, nitro, alkanyl, alkoxy, —$NH_2$ or by —$N(alkanyl)_2$, where the polysubstitution can take place by the same or by different substituents. Preferably, "alkylene" or "alkylene bridge" represents a straight-chain, saturated aliphatic radical having 1, 2, 3, 4, 5, 6 carbon atoms, which is unsubstituted or mono- or disubstituted by methyl, in particular —CH$_2$—CH$_2$—, —CH$_2$—CH$_2$—CH$_2$—, —(CH$_2$)$_4$— and —CH$_2$C(CH$_3$)$_2$CH$_2$—.

If radicals or substituents of the compounds according to the invention or the compounds according to the invention themselves are present as optically active or stereoisomeric radicals, substituents or compounds because they have, for example, an asymmetric center, these are additionally comprised by the present invention. It is obvious here that the compounds of the general formula I according to the invention can be present in isomerically pure form, for example as pure enantiomers, diastereomers, E or Z isomers, trans or cis isomers, or as a mixture of a number of isomers in any desired ratio, for example as a racemate, E/Z isomer mixture or as a cis/trans isomer mixture.

For the protection of optionally reactive functional groups or substituents optionally contained in the molecule from undesired reactions in the reaction according to the invention and/or preceding or subsequent reaction and/or workup steps, protective groups can be employed which are removed again after reaction has taken place. Methods for the use of suitable protective groups are known to the person skilled in the art and described, for example, in T. W. Green, P. G. M. Wuts: Protective Groups in Organic Synthesis, 3rd Ed., John Wiley & Sons (1999).

EXAMPLES

The starting substances can be obtained according to generally accessible literature procedures or commercially. The reactions described are known from the literature. In addition to the customary and wells known abbreviations, the following abbreviations are used:

C: Crystalline phase; N: Nematic phase; I: Isotropic phase.

Temperatures, if not stated otherwise, are in ° C.

The determination of physical, physicochemical or electrooptical parameters is carried out according to generally known methods, such as are described, inter alia, in the booklet "Merck Liquid Crystals—Licristal®—Physical Properties of Liquid Crystals—Description of the Measurements Methods", 1998, Merck KGaA, Darmstadt.

The dielectric anisotropy $\Delta\epsilon$ is determined at 20° C. and 1 kHz. The optical anisotropy $\Delta n$ is determined at 20° C. and a wavelength of 589.3 nm.

Example A a) Preparation of 3-heptyl-3,4-dihydrochromen-2-one (6)

The preparation is carried out—as shown in the reaction scheme below—according to Houben-Weyl, Methoden der Organischen Chemie, Georg Thieme Verlag, Stuttgart, N.Y., 4th ed., 1993.

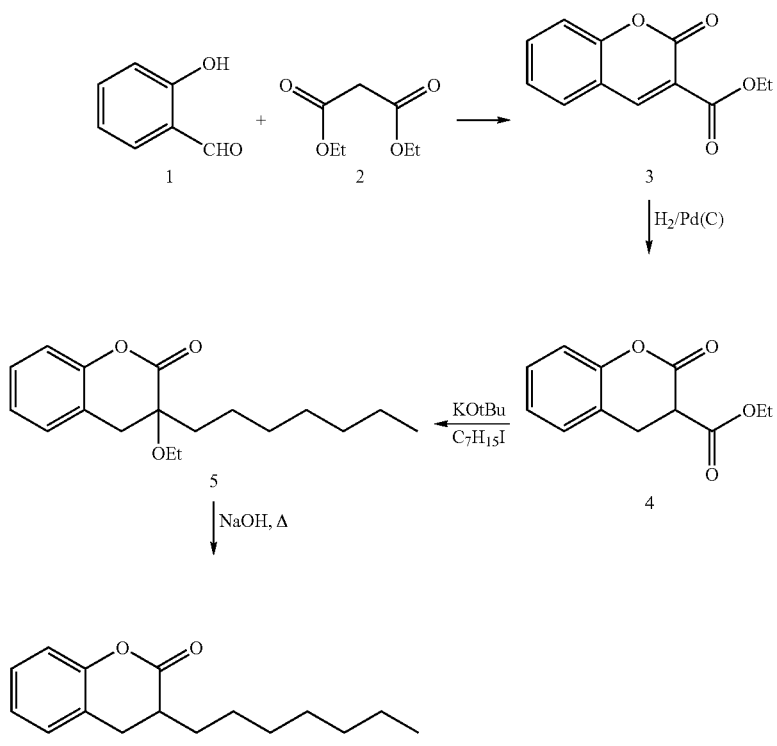

Here, the salicylaldehyde 1 is reacted under basic catalysis with diethyl malonate 2 to give the benzo-chromene 3. Hydrogenation under heterogeneous catalysis affords the corresponding benzochroman derivative 4, which is converted into 5 with n-heptyl iodide under basic catalysis. Hydrolysis and decarboxylation finally afford the lactone 6.)

b) Preparation of 15-heptyl-7-oxa-1,5-dithia-[8,13]-enzospiro[5.5]undecane (7)

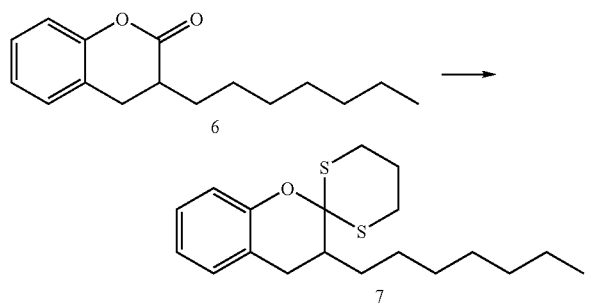

29 ml (58 mmol) of a 2 M solution of trimethylaluminum in heptane are initially introduced into 50 ml of dichloromethane under nitrogen, cooled to −75° C., and a solution of 2.9 ml (28.9 mmol) of 1,3-propanedithiol in 15 ml of dichloromethane is added dropwise. The mixture is allowed to thaw and is cooled to −20° C., and a solution of 6.80 g (27.6 mmol) of 3-heptyl-3,4-dihydrochromen-2-one (6) in 35 ml of dichloromethane is added dropwise. The mixture is stirred at room temperature overnight, added to ice water and extracted with dichloromethane. The combined organic phases are washed with water and dried over sodium sulfate. The solvent is removed in vacuo, and the residue is filtered through silica gel using heptane/methyl tert-butyl ether (MTBE) (8:2). 7.20 g (79%) of dithio-orthoester 7 are obtained as a yellow oil, which is employed in the next stage without further purification.

c) 2,2-Difluoro-3-heptyl-3,4-dihydro-2H-chromene (8)

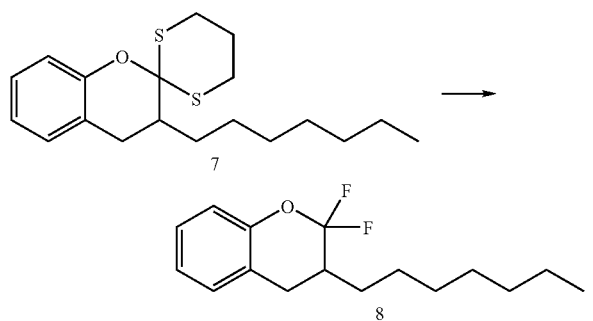

7.20 g (21.4 mmol) of dithioorthoester 7 and 17.5 ml (109 mmol) of triethylamine tris(hydrofluoride) are initially introduced at −70° C. into 120 ml of dichloromethane and subsequently treated in portions with a suspension of 31.0 g (109 mmol) of DBH in 80 ml of dichloromethane. After 2 h, the mixture is warmed to −30° C. and the orange-colored suspension is then added to a mixture of 44 ml of sodium hydrogensulfite solution and 400 ml of ice-cold 2 N sodium hydroxide solution. The aqueous phase is separated off and extracted twice with dichloromethane. The combined organic phases are washed with water, dried over sodium sulfate and purified by chromatography on silica gel. 1.7 g (30%) of 2,2-difluoro-3-heptyl-3,4-dihydro-2H-chromene (8) are obtained as a colorless liquid.

$^{19}$F-NMR (282 MHz, CDCl$_3$) δ=−74.0 ppm (ddd, $_3J_{F,H}$=2.2 Hz, $^3J_{F,H}$=3.8 Hz, $^2J_{F,F}$=154 Hz, 1 F, CF$_2$O), −79.1 (ddd, $^3J_{F,H}$=3.0 Hz, $^3J_{F,H}$=13.0 Hz, $^2J_{F,F}$=154 Hz, 1 F, CF$_2$O).

Example B a) 3-Fluoro-4-butoxy-2-hydroxybenzaldehyde (11)

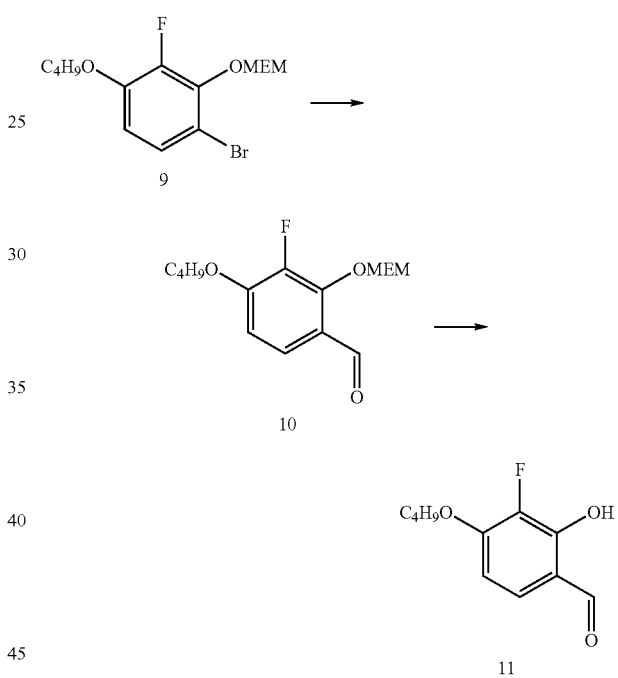

21.0 g (59.3 mmol) of 1-bromo-4-butoxy-3-fluoro-2-(2-methoxyethoxymethoxy)benzene (9) are dissolved in 200 ml of THF and treated at −78° C. with 37 ml (60 mmol) of a 15% strength solution of n-butyllithium in hexane. After 1 h, 6.8 ml (61 mmol) of N-formylpiperidine are added dropwise in 50 mmol of THF. The mixture is subsequently stirred for 1 h, and the mixture is allowed to thaw. After hydrolysis, the solution is acidified and extracted with MTBE. The combined organic phases are washed with water and dried over sodium sulfate. The solvent is removed in vacuo, the residue is taken up in 150 ml of THF, and after addition of 30 ml of conc. hydrochloric acid the mixture is stirred at room temperature overnight. The mixture is taken up in MTBE and washed with water (pH 5). The solvent is removed in vacuo and the crude product is filtered through silica gel using MTBE. 8.80 g (53%, 2 stages) of 3-fluoro-4-butoxy-2-hydroxybenzaldehyde (11) are obtained as a slightly violet solid.

b) 7-Butoxy-8-fluoro-3-[4-(4-trans-pentylcyclohexyl)-phenyl]chromen-2-one (13)

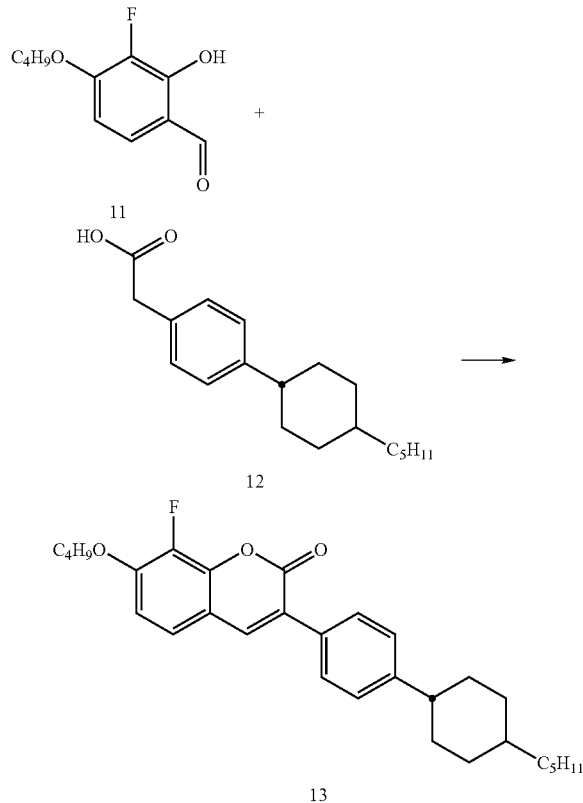

8.60 g (37.4 mmol) of 3-fluoro-4-butoxy-2-hydroxybenzaldehyde (11), 10.7 g (37.1 mmol) of 4-trans-pentyl-(4-cyclohexylphenyl)acetic acid (12), 5.2 ml (37.4 mmol) of triethylamine and 18 ml (190 mmol) of acetic anhydride are heated under reflux for 24 h. The solution is added to water, extracted with MTBE, and the combined organic phases are washed with water and dried over sodium sulfate. The solvent is removed in vacuo and the residue is recrystallized from acetonitrile. 10.8 g (57%) of 7-butoxy-8-fluoro-3-[4-(4-trans-pentyl-cyclohexyl)phenyl]chromen-2-one (13) are obtained as colorless crystals.

c) 7-Butoxy-8-fluoro-3-[4-(4-trans-pentylcyclohexyl)-phenyl]chroman-2-one (14)

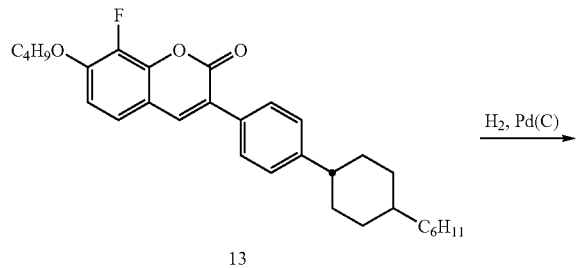

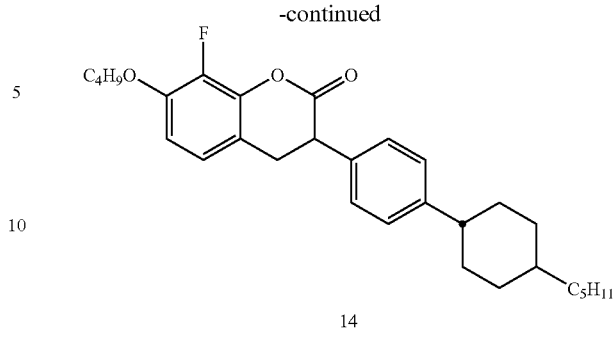

16.7 g of 7-butoxy-8-fluoro-3-[4-(4-trans-pentylcyclohexyl)phenyl]chromen-2-one (13) are hydrogenated to completion on palladium-active carbon catalyst in tetrahydrofuran. The solution is filtered and concentrated, and the residue is filtered through silica gel using toluene/heptane (2:1). 12.2 g (77%) of 7-butoxy-8-fluoro-3-[4-(4-trans-pentylcyclohexyl)phenyl]-chroman-2-one (14) are obtained as colorless crystals of melting point 145° C.

MS (EI) m/e (%)=466 [$M^+$] (100), 438 [$M^+$-CO] (74), 382 [$M^+$-CO-Bu] (84).

$^1$H-NMR (300 MHz, CDCl$_3$) δ=0.83-1.59 ppm (m, 22H), 1.73-1.94 (m, 5H), 2.45 (tt, $^3J$=3.0 Hz, $^3J$=11.5 Hz, 1H, Ar—CH(CH$_2$)$_2$, 3.18 (AB-dd, $^3J$=6.5 Hz, $^3J$=16.0 Hz, 1H, Ar—CH$_2$—CH), 3.30 (AB-dd, $^3J$=10.5 Hz, $^3J$=16.0 Hz, 1H, Ar—CH$_2$—CH), 3.94 (dd, $^3J$=6.5 Hz, $^3J$=10.5 Hz, 1H, ArCHC(O)O—Ar), 4.03 (t, $^3J$=6.6 Hz, 2H, Ar—OCH$_2$C$_3$H$_7$), 6.70 (m$_c$, 1H, Ar—H), 6.83 (m$_c$, 1H, Ar—H), 7.17 (m$_c$, 4H, Ar—H).

d) 9-Fluoro-10-butoxy-15-(4-trans-pentyl(4-cyclohexyl-phenyl))-7-oxa-1,5-dithia[8,13]benzospiro[5.5]undecane (15)

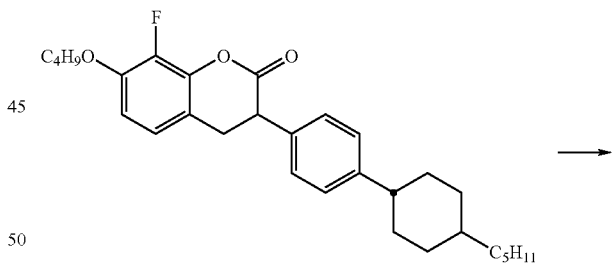

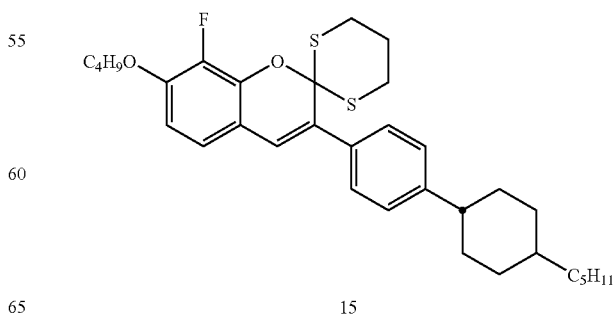

In analogy to the synthesis described above in Example A b), starting from 10.1 g of 7-butoxy-8-fluoro-3-[4-(4-trans-pentylcyclohexyl)phenyl]chroman-2-one (14), 8.7 g (70%) of 9-fluoro-10-butoxy-15-(4-trans-pentyl-(4-cyclohexylphenyl))-7-oxa-1,5-dithia[8,13]benzospiro-[5.5]undecane (15) are obtained as a colorless solid.

MS (EI) m/e (%)=556 [M⁺] (100) 460 (87).

e) 7-Butoxy-2,2,8-trifluoro-3-[4-(4-trans-pentyl cyclohexyl)phenyl]chroman (16)

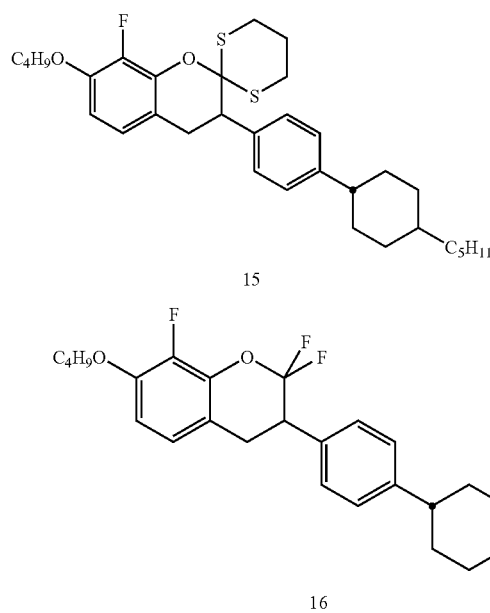

In analogy to the synthesis described in example A c), starting from 4.60 g of 9-fluoro-10-butoxy-15-(4-trans-pentyl(4-cyclohexylphenyl))-7-oxa-1,5-dithia[8,13]-benzospiro[5.5]undecane (15), 2.40 g (61%) of 7-butoxy-2,2,8-trifluoro-3-[4-(4-trans-pentylcyclohexyl)phenyl]-chroman (16) are obtained as a colorless solid.

Phase behavior: C 76 N 89.6 I. Δε=−9.3; Δn=0.1232.

$^{19}$F-NMR (282 MHz, CDCl$_3$) δ=−75.6 ppm (ddd, $_3J_{F,H}$=2.2 Hz, $^3J_{F,H}$=4.4 Hz, $^2J_{F,F}$=153 Hz, 1 F, CF$_2$O), −79.1 (dd, $^3J_{F,H}$=18.8 Hz, $^2J_{F,F}$=153 Hz, 1 F, CF$_2$O).

MS (EI) m/e (%)=488 [M⁺] (100), 432 [M⁺-Bu] (52).

Example C a) 3-Fluoro-2-benzyloxy-4-butoxybenzaldehyde (18)

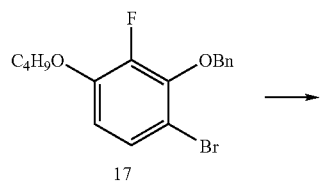

-continued

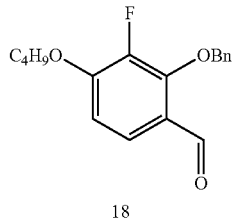

In analogy to the reaction of 9 to 10 in Example B a) above, starting from 61.6 g (0.189 mol) of 1-bromo-2-benzyloxy-4-butoxy-3-fluorobenzene (17), 37.5 g (70%) of 3-fluoro-2-benzyloxy-4-butoxybenzaldehyde (18) are obtained as yellow crystals.

b) Methyl 3-(2-(benzyloxy)-4-ethoxy-3-fluorophenyl)-3-hydroxy-2-(4-trans-propylcyclohexyl)propionate (20)

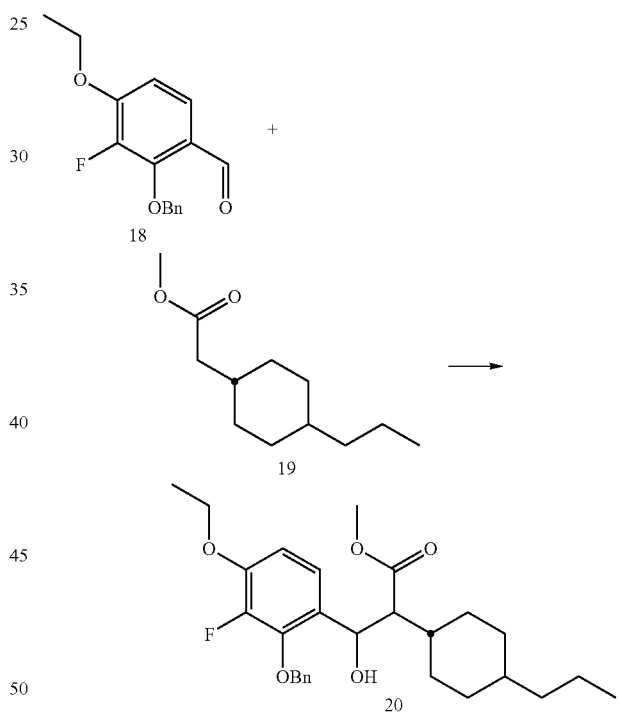

21 ml (0.149 mol) of diisopropylamine are dissolved in 300 ml of THF and 94 ml (0.149 mol) of a 15% solution of n-butyllithium in hexane are added at −78° C. The mixture is allowed to thaw and is cooled again to −78° C. Subsequently, 30.0 g (0.149 mol) of methyl (4-trans-propylcyclohexyl)acetate (19) in 300 ml of THF are added dropwise. After 2 h, a solution of 42.1 g (0.149 mol) of 3-fluoro-2-benzyloxy-4-ethoxybenzaldehyde (18) in 300 ml of THF is added dropwise, and the mixture is stirred for 2 h and warmed to −5° C. After hydrolysis, the solution is slightly acidified and extracted three times with MTBE. The combined organic phases are washed with water, the solvent is removed in vacuo and the residue is filtered through silica gel using heptane/MTBE (7:3). 51.3 g (72%) of methyl 3-(2-(benzyloxy)-4- ethoxy-3-fluorophenyl)-3-hydroxy-2-(4-transpropylcyclo-hexyl)propionate (20) are obtained as a viscous yellow oil.

MS (EI) m/e (%)=455 [M$^+$-OH] (2), 275 (70), 91 [C$_7$H$_7^+$] (100).

$^1$H-NMR (300 MHz, CDCl$_3$) δ=0.72-1.90 ppm (m, 20H), 2.64 (d, $^3$J=6.2 Hz, 1H, OH), 2.82 (dd, $^3$J=4.1 Hz, $^3$J=8.2 Hz, 1H, CHCOOMe), 3.47 (s, 3H, OCH$_3$), 4.10 (q, $^3$J=7.0 Hz, —OCH$_2$CH$_3$), 4.99 (dd, $^3$J=6.2 Hz, $^3$J=8.2 Hz, 1H, Ar—CH(OH)—), 5.11 (d, $^3$J=10.9 Hz, 1H, PhCH$_2$O—), 5.27 (d, $^3$J=11.4 Hz, 1H, PhCH$_2$O—), 6.64 (t, $^3$J=8.2 Hz, 1H, Ar—H), 6.97 (dd, $^3$J=1.8 Hz, $^3$J=8.6 Hz, 1H, Ar—H), 7.42 (m$_c$, 5H, Ar—H).

c) Methyl 3-(2-(benzyloxy)-4-ethoxy-3-fluorophenyl)-2-(4-trans-propylcyclohexyl)acrylate (21)

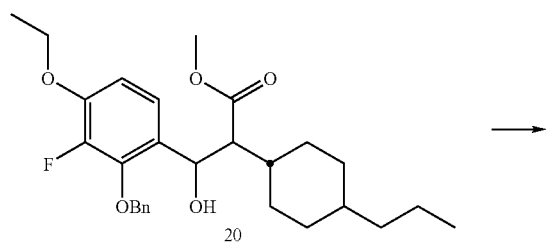

50.0 g (0.106 mol) of methyl 3-(2-(benzyloxy)-4-ethoxy-3-fluorophenyl)-3-hydroxy-2-(4-trans-propylcyclohexyl)-propionate (20) are dissolved in 500 ml of dichloro-methane and, after addition of 44 ml (0.317 mol) of triethylamine and 240 mg of N,N-dimethylaminopyridine, treated with 9.0 ml (116 mmol) of mesyl chloride with ice cooling. Subsequently, the cooling is removed and the mixture is heated under reflux for 1 h. The solution is washed three times with water and dried over sodium sulfate. The solvent is removed in vacuo and the residue is filtered through silica gel using heptane/MTB ether (8:2). 31.6 g (56%) of methyl 3-(2-(benzyloxy)-4-ethoxy-3-fluorophenyl)-2-(4-trans-propylcyclohexyl)acrylate (21) are obtained as a yellow oil.

d) Methyl 3-(4-ethoxy-3-fluoro-2-hydroxyphenyl)-2-(4-trans-propylcyclohexyl)propionate (22)

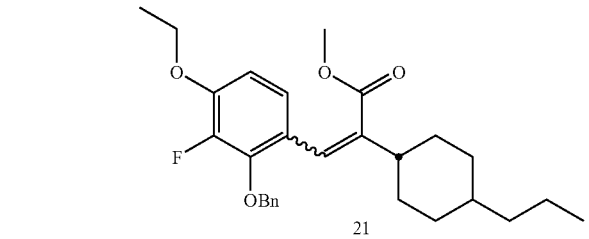

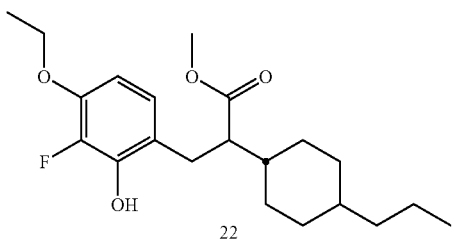

7.60 g of methyl 3-(2-(benzyloxy)-4-ethoxy-3-fluoro-phenyl)-2-(4-trans-propylcyclohexyl)acrylate (21) are hydrogenated to completion in THF on palladium-active carbon catalyst (5%). The solvent is removed in vacuo and the residue is filtered through silica gel using heptane/MTBE (8:2). 4.60 g (76%) of methyl 3-(4-ethoxy-3-fluoro-2-hydroxyphenyl)-2-(4-trans-propylcyclohexyl)-propionate (22) are obtained as colorless crystals.

e) 7-Ethoxy-8-fluoro-3-(4-trans-propylcyclohexyl)-chroman-2-one (23)

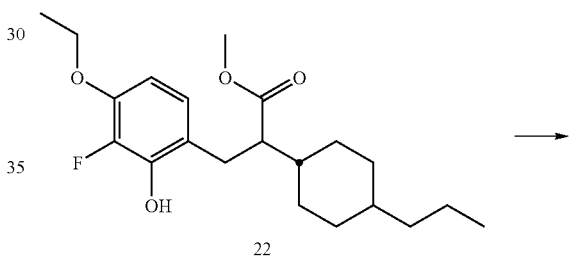

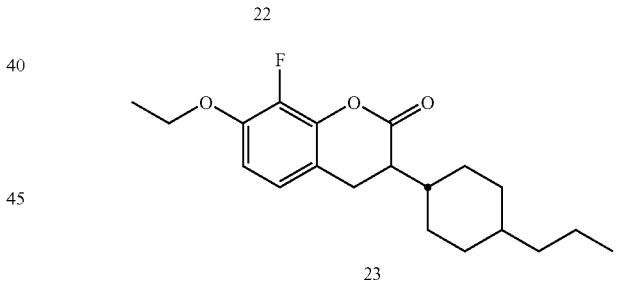

14.5 g (37.3 mmol) of methyl 3-(4-ethoxy-3-fluoro-2-hydroxyphenyl)-2-(4-trans-propylcyclohexyl)propionate (22) are dissolved in 60 ml of diphenyl ether and heated under reflux for 2 h. The mixture is added to 100 g of silica gel and the diphenyl ether is eluted using heptane. Subsequently, by diluting with heptane/MTBE (9:1), 9.10 g (72%) of 7-ethoxy-8-fluoro-3-(4-trans-propylcyclohexyl)chroman-2-one (23) are obtained as colorless flakes.

MS (EI) m/e (%)=334 [M$^+$] (84), 170 (100).

$^1$H-NMR (300 MHz, CDCl$_3$) δ=0.78-1.35 (m, 12H), 1.44 (t, $^3$J=7.1 Hz, 3H, CH$_3$), 1.65-1.85 (m, 5H), 2.54 (m$_c$, 1H, CH), 2.87 (AB-dd, $^3$J=8.3 Hz, $^2$J=15.9 Hz, 1H, ArCH$_2$), 2.95 (AB-dd, $^3$J=6.5 Hz, $^2$J=15.9 Hz, 1H, Ar—CH$_2$—), 4.10 (q, $^3$J=7.0 Hz, 2H, CH$_3$CH$_2$O—), 6.66 (dd, $^3$J=7.27 Hz, 1H, Ar—H), 6.81 (m$_c$, 1H, Ar—H3).

f) 10-Ethoxy-9-fluoro-15-(4-trans-propylcyclohexyl)-7-oxa-1,5-dithia[8,13]benzospiro[5.5]undecane (24)

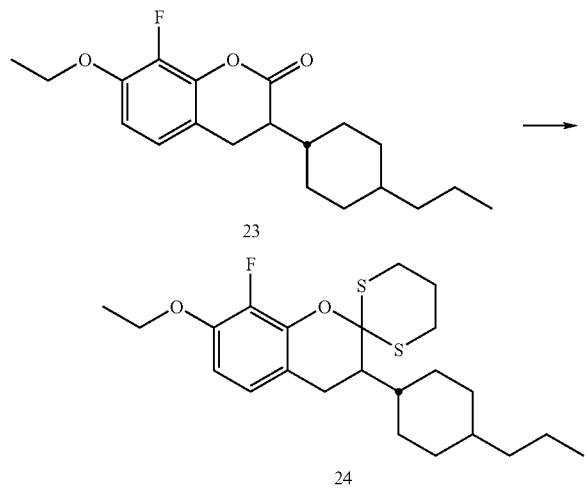

In analogy to the synthesis described in Example A b), starting from 9.10 g (26.9 mmol) of 7-ethoxy-8-fluoro-3-(4-trans-propylcyclohexyl)chroman-2-one (23), 5.60 g (49%) of 10-ethoxy-9-fluoro-15-(4-trans-propylcyclo-hexyl)-7-oxa-1,5-dithia[8,13]benzospiro[5.5]undecane (24) are obtained as a colorless solid.

MS (EI) m/e (%)=424 [M$^+$] (100), 256 (70).

g) 7-Ethoxy-2,2,8-trifluoro-3-(4-trans-propylcyclo hexyl)chroman (25)

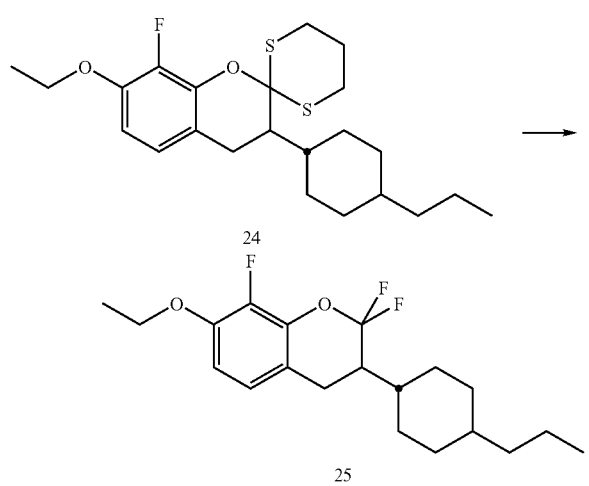

In analogy to the synthesis described in Example A c) starting front 5.60 g (13.2 mmol) of 10-ethoxy-9-fluoro-15-(4-trans-propylcyclohexyl)-7-oxa-1,5-dithia[8,13]-benzospiro[5.5]undecane (24), 1.80 g (38%) of 7-ethoxy-2,2,8-trifluoro-3-(4-trans-propylcyclohexyl)chroman (25) are obtained as a colorless solid.

Phase behavior C 81 N (−6) I. Δ∈=−11.1; Δn=0.0728.
MS (EI) m/e (%)=356 [M$^+$] (100), 328 [M$^+$-C$_2$H$_5$] (45).
$^1$H-NMR (250 MHz, CDCl$_3$) δ=0.80-1.37 ppm (m, 12H), 1.42 (t, $^3$J=7.0 Hz, 3H, CH$_3$), 1.80 (m$_c$, 5H) 2.40 (m$_c$, 1H, Ar—CH$_2$—), 2.84 (m$_c$, 2H, Ar—CH$_2$— and —CHCF$_2$O) 4.09 (q, $^3$J=7.0 Hz, 2H, OCH$_2$CH$_3$), 6.61 (dd, $^3$J=6.4 Hz, $^3$J=8.5 Hz, 1H, Ar—H), 6.67 (m$_c$, 1H, Ar—H).
$^{19}$F-NMR (235 MHz, CDCl$_3$) δ=−74.0 ppm (dd, $^3$J$_{F,H}$=2.6 Hz, $^2$J$_{F,F}$=152 Hz, 1 F, CF$_2$O), −75.9 (dd, $^3$J$_{F,H}$=19.2 Hz, $^2$J$_{F,F}$=152 Hz, 1 F, CF$_2$O), −157 (dd, $^3$J$_{F,H}$=1.5 Hz, $^3$J$_{F,H}$=7.2 Hz, 1 F, Ar—F).

Example D a1) 6-Oxa-1,4-dithia[7,8]benzospiro[4.5]decane (27)

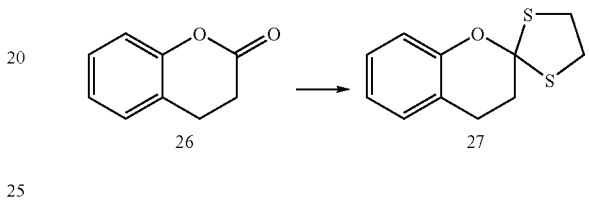

236 ml (0.472 mol) of a 2 M solution of trimethyl-aluminum in heptane are initially introduced at −78° C., and a solution of 19.9 ml (0.236 mol) of ethanedithiol in 20 ml of dichloromethane is added. The mixture is allowed to thaw and is cooled to −20° C. and a solution of 35.0 g (0.236 mol) of dihydrocoumarin (26) in 330 ml of dichloromethane is added dropwise. The mixture is stirred overnight at room temperature, ice is added and it is acidified with conc. hydrochloric acid. The aqueous phase is separated off and extracted with dichloromethane. The combined organic phases are washed with water, dried over sodium sulfate and concentrated. After filtration of the crude product using heptane/MTB ether (2:1) on silica gel, 44.5 g (84%) of dithio-orthoester 27 are obtained as a colorless oil.

MS (EI): m/e (%)=223 (100) [M$^+$-H].
$^1$H-NMR (300 MHz, CDCl$_3$) δ=2.62 ppm (t, $^3$J=6.7 Hz, 2H, ArCH$_2$CH$_2$), 3.02 (t, $^3$J=6.7 Hz, 2H, ArCH$_2$CH$_2$), 3.53 (m$_c$, 4H, —SCH$_2$CH$_2$S—), 6.87 (m$_c$, 2H, Ar—H), 7.11 (m$_c$, 2H, Ar—H).

a2) 7-Oxa-1,5-dithia[8,9]benzospiro[5.5]undecane (31)

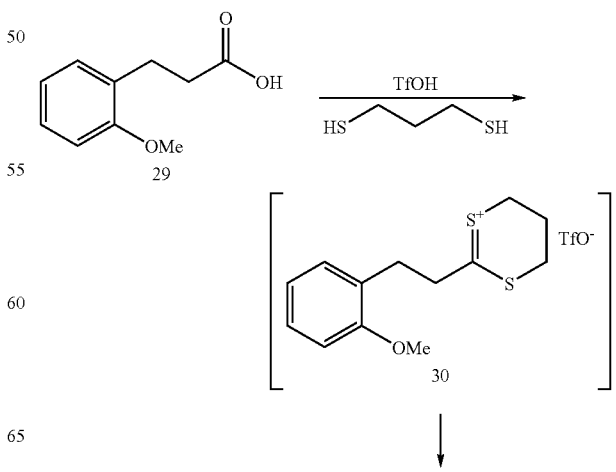

-continued

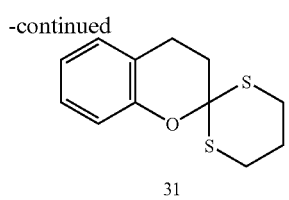

31

10 g (55.5 mmol) of o-methoxyphenylpropionic acid (29) and 6.1 ml of 1,3-propanedithiol are initially introduced and, after addition of 14.6 ml (0.167 mol) of trifluoromethanesulfonic acid, heated at 120° C. for 2 h. The reaction mixture is added to sodium hydroxide solution with cooling, extracted with toluene, and the combined organic phases are dried over sodium sulfate. The solvent is removed in vacuo and the residue is filtered through silica gel using 1-chlorobutane. 6.48 g (49%) of spiro compound 31 are obtained as a yellow oil.

MS (EI) m/e (%)=238 (100) [M$^+$].

$^1$H-NMR (300 MHz, CDCl$_3$) δ=2.07 ppm (m$_c$, 1H, —SCH$_2$CH$_2$CH$_2$S—) 2.25 (m$_c$, 1H, —SCH$_2$C$_1$H$_2$CH$_2$S—) 2.32 (t, J=7.0 Hz, 2H, Ar—CH$_2$CH$_2$—), 2.71 (dt, J=14.4 Hz, J=3.4 Hz, 2H, —SCH$_2$CH$_2$CH$_2$S—), 2.97 (t, J=7.0 Hz, 2H, Ar—CH$_2$—CH$_2$), 3.64 (m$_c$, 2H, —SCH$_2$CH$_2$CH$_2$S—), 6.92 (m$_c$, 2H, Ar—H), 7.08 (d, J=7.6 Hz, 1H, Ar—H), 7.13 (m$_c$, therein: t, J=7.6 Hz, 1H, Ar—H).

B) 2,2-Difluorochroman (32)

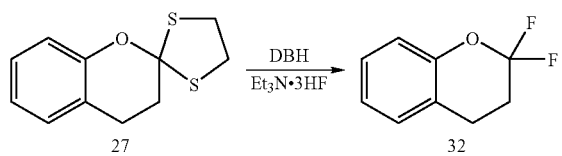

5.00 g (22.3 mmol) of dithioorthoester 27 are dissolved in 120 ml of dichloromethane and first treated with 18 ml (0.111 mol) of triethylamine trishydrofluoride at −75° C. Subsequently, a suspension of 31.9 g (0.111 mol) of 1,3-dibromo-5,5-dimethylhydantoin are added in portions in 50 ml of dichloromethane in the course of 30 min. The mixture is stirred for a further 2.5 h, warmed to room temperature, hydrolyzed using 1 N sodium hydroxide solution and extracted three times with dichloromethane. The combined organic phases are dried over sodium sulfate, concentrated and the crude product is filtered through silica gel using n-heptane/ethyl acetate (50:1). The product is further purified by bulb tube distillation. 2.80 g (74%) of the target compound 32, a slightly yellow liquid, are obtained, Content: 99.2% (GC).

Analogously, 32 can also be prepared from compound 31 (Example D a2)).

$^1$H-NMR (300 MHz, CDCl$_3$) δ=2.32 ppm (tt, $^3$J$_{F,H}$=8.9 Hz, $^3$J$_{H,H}$=7.1 Hz, 2H, CH$_2$), 2.96 (t, $^3$J$_{H,H}$=7.1 Hz, 2H, CH$_2$), 6.99 (m$_c$, 2H, Ar—H), 7.18 (m$_c$, 2H, Ar—H).

$^{13}$C-NMR (75 MHz, CDCl$_3$)=δ=22.54 (t, $^3$J$_{C,F}$=4.0 Hz, CH$_2$CH$_2$CF$_2$), 27.88 (t, $^2$J$_{C,F}$=29.1 Hz, CH$_2$CH$_2$CF$_2$), 116.85 (CH), 120.47 (C) 123.03 (CH)/123.16 (t, $^1$J$_{C,F}$=255 Hz, CF$_2$O), 128.15 (CH), 128.78 (CH), 150.95 (C).

$^{19}$F-NMR (282 MHz, CDCl$_3$) δ=−69.77 ppm (t, $^3$J$_{F,H}$=8.9 Hz, 2 F, CF$_2$).

MS (EI) m/e (%)=170 (100) [M$^+$], 150 (7) [M$^+$-HF].
HR-MS (EI) calc.: m/e=170.054716; fnd: m/e 170.054321.

Example E

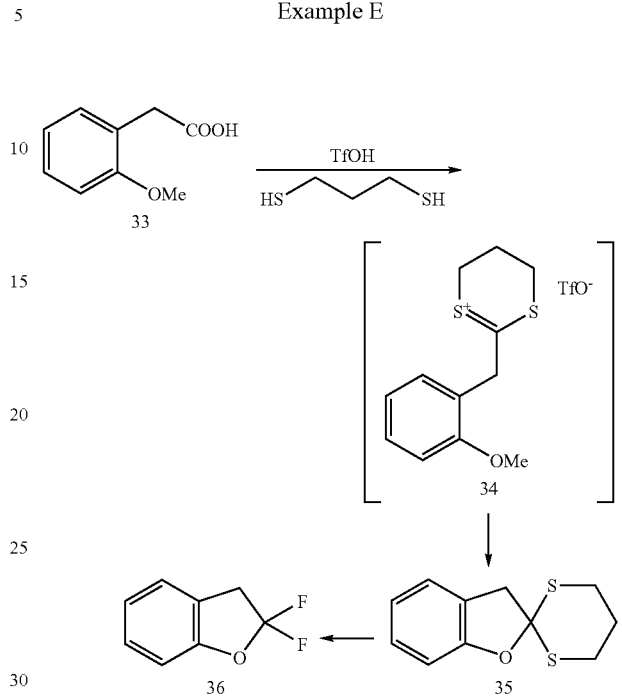

Analogously to Example D, starting from (2-methoxyphenyl)acetic acid (33), 2,2-difluoro-2,3-dihydrobenzofuran (36) is obtained as a colorless liquid.

$^1$H-NMR (300 MHz, CDCl$_3$) δ=3.59 ppm (t, $^3$J$_{F,H}$=14.0 Hz, 2H, CH$_2$), 6.96 (d, J=8.1 Hz, 1H, Ar—H), 7.04 (dd, J=0.9 Hz, J=7.5 Hz, 1H, Ar—H), 7.22 (m$_c$, 2H, Ar—H).

$^{19}$F-NMR (235 MHz, CDCl$_3$) δ=−63.94 ppm (t, $^3$J$_{F,H}$=14.0 Hz, 2 F, CF$_2$)

MS (EI) m/e (%)=156 (100) [M$^+$], 136 (6) [M$^+$-HF].

The following compounds according to the invention are prepared in analogy to the examples A-E described above.

The following are prepared analogously to Example A:

Example 1-105

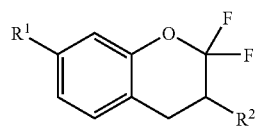

Example 106-210

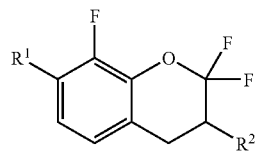

Example 316-420

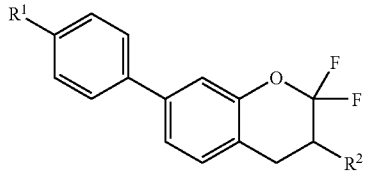

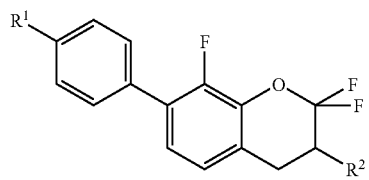

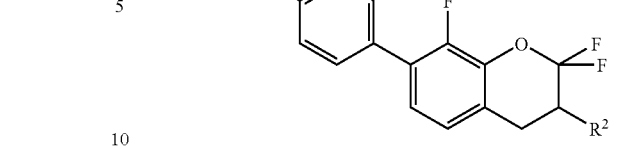

| Example No. | | | | R¹ | R² |
|---|---|---|---|---|---|
| 1, | 106, | 211, | 316 | H | CH₃ |
| 2, | 107, | 212, | 317 | H | C₂H₅ |
| 3, | 108, | 213, | 318 | H | n-C₃H₇ |
| 4, | 109, | 214, | 319 | H | n-C₄H₉ |
| 5, | 110, | 215, | 320 | H | n-C₅H₁₁ |
| 6, | 111, | 216, | 321 | H | n-C₆H₁₃ |
| 7, | 112, | 217, | 322 | H | n-C₇H₁₅ |
| 8, | 113, | 218, | 323 | CH₃ | CH₃ |
| 9, | 114, | 219, | 324 | CH₃ | C₂H₅ |
| 10, | 115, | 220, | 325 | CH₃ | n-C₃H₇ |
| 11, | 116, | 221, | 326 | CH₃ | n-C₄H₉ |
| 12, | 117, | 222, | 327 | CH₃ | n-C₅H₁₁ |
| 13, | 118, | 223, | 328 | CH₃ | n-C₆H₁₃ |
| 14, | 119, | 224, | 329 | CH₃ | n-C₇H₁₅ |
| 15, | 120, | 225, | 330 | C₂H₅ | CH₃ |
| 16, | 121, | 226, | 331 | C₂H₅ | C₂H₅ |
| 17, | 122, | 227, | 332 | C₂H₅ | n-C₃H₇ |
| 18, | 123, | 228, | 333 | C₂H₅ | n-C₄H₉ |
| 19, | 124, | 229, | 334 | C₂H₅ | n-C₅H₁₁ |
| 20, | 125, | 230, | 335 | C₂H₅ | n-C₆H₁₃ |
| 21, | 126, | 231, | 336 | C₂H₅ | n-C₇H₁₅ |
| 22, | 127, | 232, | 337 | n-C₃H₇ | CH₃ |
| 23, | 128, | 233, | 338 | n-C₃H₇ | C₂H₅ |
| 24, | 129, | 234, | 339 | n-C₃H₇ | n-C₃H₇ |
| 25, | 130, | 235, | 340 | n-C₃H₇ | n-C₄H₉ |
| 26, | 131, | 236, | 341 | n-C₃H₇ | n-C₅H₁₁ |
| 27, | 132, | 237, | 342 | n-C₃H₇ | n-C₆H₁₃ |
| 28, | 133, | 238, | 343 | n-C₃H₇ | n-C₇H₁₅ |
| 29, | 134, | 239, | 344 | n-C₄H₉ | CH₃ |
| 30, | 135, | 240, | 345 | n-C₄H₉ | C₂H₅ |
| 31, | 136, | 241, | 346 | n-C₄H₉ | n-C₃H₇ |
| 32, | 137, | 242, | 347 | n-C₄H₉ | n-C₄H₉ |
| 33, | 138, | 243, | 348 | n-C₄H₉ | n-C₅H₁₁ |
| 34, | 139, | 244, | 349 | n-C₄H₉ | n-C₆H₁₃ |
| 35, | 140, | 245, | 350 | n-C₄H₉ | n-C₇H₁₅ |
| 36, | 141, | 246, | 351 | n-C₅H₁₁ | CH₃ |
| 37, | 142, | 247, | 352 | n-C₅H₁₁ | C₂H₅ |
| 38, | 143, | 248, | 353 | n-C₅H₁₁ | n-C₃H₇ |
| 39, | 144, | 249, | 354 | n-C₅H₁₁ | n-C₄H₉ |
| 40, | 145, | 250, | 355 | n-C₅H₁₁ | n-C₅H₁₁ |
| 41, | 146, | 251, | 356 | n-C₅H₁₁ | n-C₆H₁₃ |
| 42, | 147, | 252, | 357 | n-C₅H₁₁ | n-C₇H₁₅ |
| 43, | 148, | 253, | 358 | n-C₆H₁₃ | CH₃ |
| 44, | 149, | 254, | 359 | n-C₆H₁₃ | C₂H₅ |
| 45, | 150, | 255, | 360 | n-C₆H₁₃ | n-C₃H₇ |
| 46, | 151, | 256, | 361 | n-C₆H₁₃ | n-C₄H₉ |
| 47, | 152, | 257, | 362 | n-C₆H₁₃ | n-C₅H₁₁ |
| 48, | 153, | 258, | 363 | n-C₆H₁₃ | n-C₆H₁₃ |
| 49, | 154, | 259, | 364 | n-C₆H₁₃ | n-C₇H₁₅ |
| 50, | 155, | 260, | 365 | n-C₇H₁₅ | CH₃ |
| 51, | 156, | 261, | 366 | n-C₇H₁₅ | C₂H₅ |
| 52, | 157, | 262, | 367 | n-C₇H₁₅ | n-C₃H₇ |
| 53, | 158, | 263, | 368 | n-C₇H₁₅ | n-C₄H₉ |
| 54, | 159, | 264, | 369 | n-C₇H₁₅ | n-C₅H₁₁ |
| 55, | 160, | 265, | 370 | n-C₇H₁₅ | n-C₆H₁₃ |
| 56, | 161, | 266, | 371 | n-C₇H₁₅ | n-C₇H₁₅ |
| 57, | 162, | 267, | 372 | OCH₃ | CH₃ |
| 58, | 163, | 268, | 373 | OCH₃ | C₂H₅ |
| 59, | 164, | 269, | 374 | OCH₃ | n-C₃H₇ |
| 60, | 165, | 270, | 375 | OCH₃ | n-C₄H₉ |
| 61, | 166, | 271, | 376 | OCH₃ | n-C₅H₁₁ |
| 62, | 167, | 272, | 377 | OCH₃ | n-C₆H₁₃ |
| 63, | 168, | 273, | 378 | OCH₃ | n-C₇H₁₅ |
| 64, | 169, | 274, | 379 | OC₂H₅ | CH₃ |
| 65, | 170, | 275, | 380 | OC₂H₅ | C₂H₅ |
| 66, | 171, | 276, | 381 | OC₂H₅ | n-C₃H₇ |
| 67, | 172, | 277, | 382 | OC₂H₅ | n-C₄H₉ |
| 68, | 173, | 278, | 383 | OC₂H₅ | n-C₅H₁₁ |
| 69, | 174, | 279, | 384 | OC₂H₅ | n-C₆H₁₃ |
| 70, | 175, | 280, | 385 | OC₂H₅ | n-C₇H₁₅ |
| 71, | 176, | 281, | 386 | O-n-C₃H₇ | CH₃ |
| 72, | 177, | 282, | 387 | O-n-C₃H₇ | C₂H₅ |
| 73, | 178, | 283, | 388 | O-n-C₃H₇ | n-C₃H₇ |
| 74, | 179, | 284, | 389 | O-n-C₃H₇ | n-C₄H₉ |
| 75, | 180, | 285, | 390 | O-n-C₃H₇ | n-C₅H₁₁ |
| 76, | 181, | 286, | 391 | O-n-C₃H₇ | n-C₆H₁₃ |
| 77, | 182, | 287, | 392 | O-n-C₃H₇ | n-C₇H₁₅ |
| 78, | 183, | 288, | 393 | O-n-C₄H₉ | CH₃ |
| 79, | 184, | 289, | 394 | O-n-C₄H₉ | C₂H₅ |
| 80, | 185, | 290, | 395 | O-n-C₄H₉ | n-C₃H₇ |
| 81, | 186, | 291, | 396 | O-n-C₄H₉ | n-C₄H₉ |
| 82, | 187, | 292, | 397 | O-n-C₄H₉ | n-C₅H₁₁ |
| 83, | 188, | 293, | 398 | O-n-C₄H₉ | n-C₆H₁₃ |
| 84, | 189, | 294, | 399 | O-n-C₄H₉ | n-C₇H₁₅ |
| 85, | 190, | 295, | 400 | O-n-C₅H₁₁ | CH₃ |
| 86, | 191, | 296, | 401 | O-n-C₅H₁₁ | C₂H₅ |
| 87, | 192, | 297, | 402 | O-n-C₅H₁₁ | n-C₃H₇ |
| 88, | 193, | 298, | 403 | O-n-C₅H₁₁ | n-C₄H₉ |
| 89, | 194, | 299, | 404 | O-n-C₅H₁₁ | n-C₅H₁₁ |
| 90, | 195, | 300, | 405 | O-n-C₅H₁₁ | n-C₆H₁₃ |
| 91, | 196, | 301, | 406 | O-n-C₅H₁₁ | n-C₇H₁₅ |
| 92, | 197, | 302, | 407 | O-n-C₆H₁₃ | CH₃ |
| 93, | 198, | 303, | 408 | O-n-C₆H₁₃ | C₂H₅ |
| 94, | 199, | 304, | 409 | O-n-C₆H₁₃ | n-C₃H₇ |
| 95, | 200, | 305, | 410 | O-n-C₆H₁₃ | n-C₄H₉ |
| 96, | 201, | 306, | 411 | O-n-C₆H₁₃ | n-C₅H₁₁ |
| 97, | 202, | 307, | 412 | O-n-C₆H₁₃ | n-C₆H₁₃ |
| 98, | 203, | 308, | 413 | O-n-C₆H₁₃ | n-C₇H₁₅ |
| 99, | 204, | 309, | 414 | O-n-C₇H₁₅ | CH₃ |
| 100, | 205, | 310, | 415 | O-n-C₇H₁₅ | C₂H₅ |
| 101, | 206, | 311, | 416 | O-n-C₇H₁₅ | n-C₃H₇ |
| 102, | 207, | 312, | 417 | O-n-C₇H₁₅ | n-C₄H₉ |
| 103, | 208, | 313, | 418 | O-n-C₇H₁₅ | n-C₅H₁₁ |
| 104, | 209, | 314, | 419 | O-n-C₇H₁₅ | n-C₆H₁₃ |
| 105, | 210, | 315, | 420 | O-n-C₇H₁₅ | n-C₇H₁₅ |

Measurements for selected examples:

Example No. 338

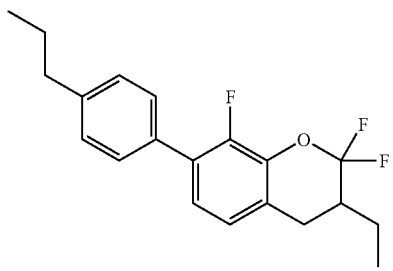

Phase behavior: C 108 I. Δε=−5.9; Δn=0.099.
The following are prepared analogously to Example A:

Example 421-476

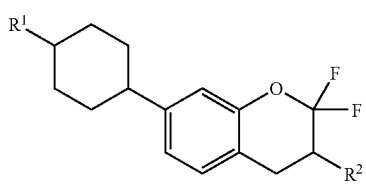

Example 477-532

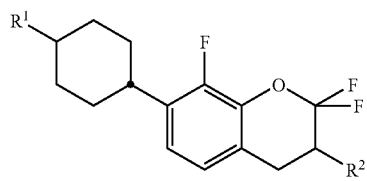

| Example No. | | $R^1$ | $R^2$ |
|---|---|---|---|
| 421, | 477, | H | $CH_3$ |
| 422, | 478, | H | $C_2H_5$ |
| 423, | 479, | H | $n-C_3H_7$ |
| 424, | 480, | H | $n-C_4H_9$ |
| 425, | 481, | H | $n-C_5H_{11}$ |
| 426, | 482, | H | $n-C_6H_{13}$ |
| 427, | 483, | H | $n-C_7H_{15}$ |
| 428, | 484, | $CH_3$ | $CH_3$ |
| 429, | 485, | $CH_3$ | $C_2H_5$ |
| 430, | 486, | $CH_3$ | $n-C_3H_7$ |
| 431, | 487, | $CH_3$ | $n-C_4H_9$ |
| 432, | 488, | $CH_3$ | $n-C_5H_{11}$ |
| 433, | 489, | $CH_3$ | $n-C_6H_{13}$ |
| 434, | 490, | $CH_3$ | $n-C_7H_{15}$ |
| 435, | 491, | $C_2H_5$ | $CH_3$ |
| 436, | 492, | $C_2H_5$ | $C_2H_5$ |
| 437, | 493, | $C_2H_5$ | $n-C_3H_7$ |
| 438, | 494, | $C_2H_5$ | $n-C_4H_9$ |
| 439, | 495, | $C_2H_5$ | $n-C_5H_{11}$ |
| 440, | 496, | $C_2H_5$ | $n-C_6H_{13}$ |
| 441, | 497, | $C_2H_5$ | $n-C_7H_{15}$ |
| 442, | 498, | $n-C_3H_7$ | $CH_3$ |
| 443, | 499, | $n-C_3H_7$ | $C_2H_5$ |
| 444, | 500, | $n-C_3H_7$ | $n-C_3H_7$ |

-continued

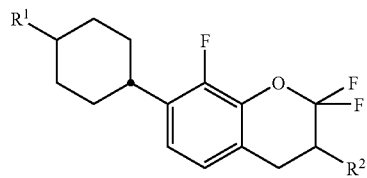

| Example No. | | $R^1$ | $R^2$ |
|---|---|---|---|
| 445, | 501, | $n-C_3H_7$ | $n-C_4H_9$ |
| 446, | 502, | $n-C_3H_7$ | $n-C_5H_{11}$ |
| 447, | 503, | $n-C_3H_7$ | $n-C_6H_{13}$ |
| 448, | 504, | $n-C_3H_7$ | $n-C_7H_{15}$ |
| 449, | 505, | $n-C_4H_9$ | $CH_3$ |
| 450, | 506, | $n-C_4H_9$ | $C_2H_5$ |
| 451, | 507, | $n-C_4H_9$ | $n-C_3H_7$ |
| 452, | 508, | $n-C_4H_9$ | $n-C_4H_9$ |
| 453, | 509, | $n-C_4H_9$ | $n-C_5H_{11}$ |
| 454, | 510, | $n-C_4H_9$ | $n-C_6H_{13}$ |
| 455, | 511, | $n-C_4H_9$ | $n-C_7H_{15}$ |
| 456, | 512, | $n-C_5H_{11}$ | $CH_3$ |
| 457, | 513, | $n-C_5H_{11}$ | $C_2H_5$ |
| 458, | 514, | $n-C_5H_{11}$ | $n-C_3H_7$ |
| 459, | 515, | $n-C_5H_{11}$ | $n-C_4H_9$ |
| 460, | 516, | $n-C_5H_{11}$ | $n-C_5H_{11}$ |
| 461, | 517, | $n-C_5H_{11}$ | $n-C_6H_{13}$ |
| 462, | 518, | $n-C_5H_{11}$ | $n-C_7H_{15}$ |
| 463, | 519, | $n-C_6H_{13}$ | $CH_3$ |
| 464, | 520, | $n-C_6H_{13}$ | $C_2H_5$ |
| 465, | 521, | $n-C_6H_{13}$ | $n-C_3H_7$ |
| 466, | 522, | $n-C_6H_{13}$ | $n-C_4H_9$ |
| 467, | 523, | $n-C_6H_{13}$ | $n-C_5H_{11}$ |
| 468, | 524, | $n-C_6H_{13}$ | $n-C_6H_{13}$ |
| 469, | 525, | $n-C_6H_{13}$ | $n-C_7H_{15}$ |
| 470, | 526, | $n-C_7H_{15}$ | $CH_3$ |
| 471, | 527, | $n-C_7H_{15}$ | $C_2H_5$ |
| 472, | 528, | $n-C_7H_{15}$ | $n-C_3H_7$ |
| 473, | 529, | $n-C_7H_{15}$ | $n-C_4H_9$ |
| 474, | 530, | $n-C_7H_{15}$ | $n-C_5H_{11}$ |
| 475, | 531, | $n-C_7H_{15}$ | $n-C_6H_{13}$ |
| 476, | 532, | $n-C_7H_{15}$ | $n-C_7H_{15}$ |

Measurements for selected examples:

Example No. 502

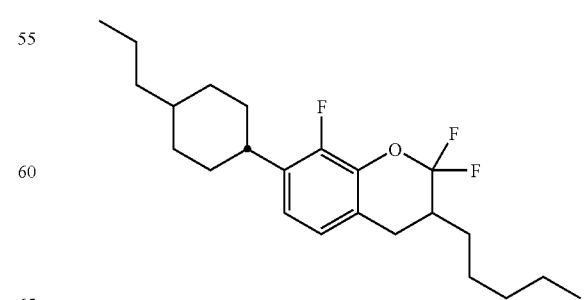

Phase behavior: C 25 I. $\Delta\epsilon=-6.6$; $\Delta n=0.047$.
The following are prepared analogously to Example B:

Example 533-637

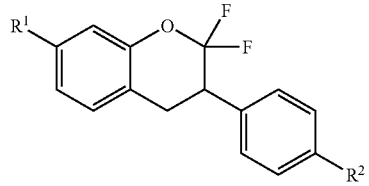

Example 638-742

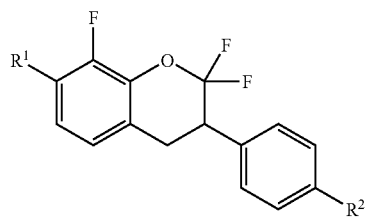

Example 743-847

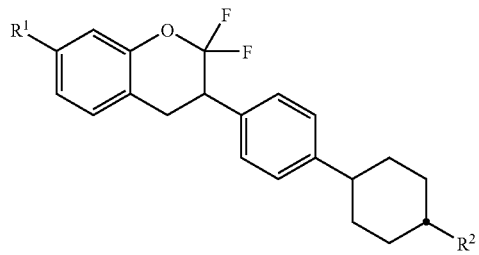

Example 848-952

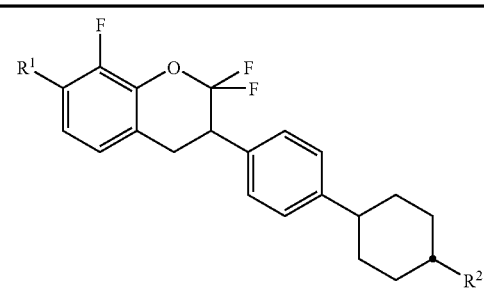

| Example No. | | | | $R^1$ | $R^2$ |
|---|---|---|---|---|---|
| 533, | 638, | 743, | 848 | H | $CH_3$ |
| 534, | 639, | 744, | 849 | H | $C_2H_5$ |
| 535, | 640, | 745, | 850 | H | n-$C_3H_7$ |
| 536, | 641, | 746, | 851 | H | n-$C_4H_9$ |
| 537, | 642, | 747, | 852 | H | n-$C_5H_{11}$ |
| 538, | 643, | 748, | 853 | H | n-$C_6H_{13}$ |
| 539, | 644, | 749, | 854 | H | n-$C_7H_{15}$ |
| 540, | 645, | 750, | 855 | $CH_3$ | $CH_3$ |
| 541, | 646, | 751, | 856 | $CH_3$ | $C_2H_5$ |
| 542, | 647, | 752, | 857 | $CH_3$ | n-$C_3H_7$ |
| 543, | 648, | 753, | 858 | $CH_3$ | n-$C_4H_9$ |
| 544, | 649, | 754, | 859 | $CH_3$ | n-$C_5H_{11}$ |
| 545, | 650, | 755, | 860 | $CH_3$ | n-$C_6H_{13}$ |
| 546, | 651, | 756, | 861 | $CH_3$ | n-$C_7H_{15}$ |
| 547, | 652, | 757, | 862 | $C_2H_5$ | $CH_3$ |
| 548, | 653, | 758, | 863 | $C_2H_5$ | $C_2H_5$ |
| 549, | 654, | 759, | 864 | $C_2H_5$ | n-$C_3H_7$ |
| 550, | 655, | 760, | 865 | $C_2H_5$ | n-$C_4H_9$ |
| 551, | 656, | 761, | 866 | $C_2H_5$ | n-$C_5H_{11}$ |
| 552, | 657, | 762, | 867 | $C_2H_5$ | n-$C_6H_{13}$ |
| 553, | 658, | 763, | 868 | $C_2H_5$ | n-$C_7H_{15}$ |
| 554, | 659, | 764, | 869 | n-$C_3H_7$ | $CH_3$ |
| 555, | 660, | 765, | 870 | n-$C_3H_7$ | $C_2H_5$ |
| 556, | 661, | 766, | 871 | n-$C_3H_7$ | n-$C_3H_7$ |
| 557, | 662, | 767, | 872 | n-$C_3H_7$ | n-$C_4H_9$ |
| 558, | 663, | 768, | 873 | n-$C_3H_7$ | n-$C_5H_{11}$ |
| 559, | 664, | 769, | 874 | n-$C_3H_7$ | n-$C_6H_{13}$ |
| 560, | 665, | 770, | 875 | n-$C_3H_7$ | n-$C_7H_{15}$ |
| 561, | 666, | 771, | 876 | n-$C_4H_9$ | $CH_3$ |
| 562, | 667, | 772, | 877 | n-$C_4H_9$ | $C_2H_5$ |
| 563, | 668, | 773, | 878 | n-$C_4H_9$ | n-$C_3H_7$ |
| 564, | 669, | 774, | 879 | n-$C_4H_9$ | n-$C_4H_9$ |
| 565, | 670, | 775, | 880 | n-$C_4H_9$ | n-$C_5H_{11}$ |
| 566, | 671, | 776, | 881 | n-$C_4H_9$ | n-$C_6H_{13}$ |
| 567, | 672, | 777, | 882 | n-$C_4H_9$ | n-$C_7H_{15}$ |
| 568, | 673, | 778, | 883 | n-$C_5H_{11}$ | $CH_3$ |
| 569, | 674, | 779, | 884 | n-$C_5H_{11}$ | $C_2H_5$ |
| 570, | 675, | 780, | 885 | n-$C_5H_{11}$ | n-$C_3H_7$ |
| 571, | 676, | 781, | 886 | n-$C_5H_{11}$ | n-$C_4H_9$ |
| 572, | 677, | 782, | 887 | n-$C_5H_{11}$ | n-$C_5H_{11}$ |
| 573, | 678, | 783, | 888 | n-$C_5H_{11}$ | n-$C_6H_{13}$ |
| 574, | 679, | 784, | 889 | n-$C_5H_{11}$ | n-$C_7H_{15}$ |
| 575, | 680, | 785, | 890 | n-$C_6H_{13}$ | $CH_3$ |
| 576, | 681, | 786, | 891 | n-$C_6H_{13}$ | $C_2H_5$ |
| 577, | 682, | 787, | 892 | n-$C_6H_{13}$ | n-$C_3H_7$ |
| 578, | 683, | 788, | 893 | n-$C_6H_{13}$ | n-$C_4H_9$ |
| 579, | 684, | 789, | 894 | n-$C_6H_{13}$ | n-$C_5H_{11}$ |
| 580, | 685, | 790, | 895 | n-$C_6H_{13}$ | n-$C_6H_{13}$ |
| 581, | 686, | 791, | 896 | n-$C_6H_{13}$ | n-$C_7H_{15}$ |
| 582, | 687, | 792, | 897 | n-$C_7H_{15}$ | $CH_3$ |
| 583, | 688, | 793, | 898 | n-$C_7H_{15}$ | $C_2H_5$ |
| 584, | 689, | 794, | 899 | n-$C_7H_{15}$ | n-$C_3H_7$ |
| 585, | 690, | 795, | 900 | n-$C_7H_{15}$ | n-$C_4H_9$ |
| 586, | 691, | 796, | 901 | n-$C_7H_{15}$ | n-$C_5H_{11}$ |
| 587, | 692, | 797, | 902 | n-$C_7H_{15}$ | n-$C_6H_{13}$ |
| 588, | 693, | 798, | 903 | n-$C_7H_{15}$ | n-$C_7H_{15}$ |
| 589, | 694, | 799, | 904 | $OCH_3$ | $CH_3$ |
| 590, | 695, | 800, | 905 | $OCH_3$ | $C_2H_5$ |
| 591, | 696, | 801, | 906 | $OCH_3$ | n-$C_3H_7$ |
| 592, | 697, | 802, | 907 | $OCH_3$ | n-$C_4H_9$ |
| 593, | 698, | 803, | 908 | $OCH_3$ | n-$C_5H_{11}$ |
| 594, | 699, | 804, | 909 | $OCH_3$ | n-$C_6H_{13}$ |
| 595, | 700, | 805, | 910 | $OCH_3$ | n-$C_7H_{15}$ |
| 596, | 701, | 806, | 911 | $OC_2H_5$ | $CH_3$ |
| 597, | 702, | 807, | 912 | $OC_2H_5$ | $C_2H_5$ |

-continued

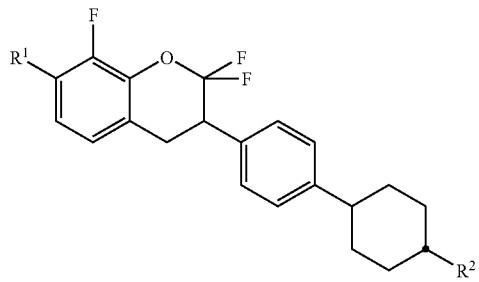

| Example No. | | | | R¹ | R² |
|---|---|---|---|---|---|
| 598, | 703, | 808, | 913 | OC₂H₅ | n-C₃H₇ |
| 599, | 704, | 809, | 914 | OC₂H₅ | n-C₄H₉ |
| 600, | 705, | 810, | 915 | OC₂H₅ | n-C₅H₁₁ |
| 601, | 706, | 811, | 916 | OC₂H₅ | n-C₆H₁₃ |
| 602, | 707, | 812, | 917 | OC₂H₅ | n-C₇H₁₅ |
| 603, | 708, | 813, | 918 | O-n-C₃H₇ | CH₃ |
| 604, | 709, | 814, | 919 | O-n-C₃H₇ | C₂H₅ |
| 605, | 710, | 815, | 920 | O-n-C₃H₇ | n-C₃H₇ |
| 606, | 711, | 816, | 921 | O-n-C₃H₇ | n-C₄H₉ |
| 607, | 712, | 817, | 922 | O-n-C₃H₇ | n-C₅H₁₁ |
| 608, | 713, | 818, | 923 | O-n-C₃H₇ | n-C₆H₁₃ |
| 609, | 714, | 819, | 924 | O-n-C₃H₇ | n-C₇H₁₅ |
| 610, | 715, | 820, | 925 | O-n-C₄H₉ | CH₃ |
| 611, | 716, | 821, | 926 | O-n-C₄H₉ | C₂H₅ |
| 612, | 717, | 822, | 927 | O-n-C₄H₉ | n-C₃H₇ |
| 613, | 718, | 823, | 928 | O-n-C₄H₉ | n-C₄H₉ |
| 614, | 719, | 824, | 929 | O-n-C₄H₉ | n-C₅H₁₁ |
| 615, | 720, | 825, | 930 | O-n-C₄H₉ | n-C₆H₁₃ |
| 616, | 721, | 826, | 931 | O-n-C₄H₉ | n-C₇H₁₅ |
| 617, | 722, | 827, | 932 | O-n-C₅H₁₁ | CH₃ |
| 618, | 723, | 828, | 933 | O-n-C₅H₁₁ | C₂H₅ |
| 619, | 724, | 829, | 934 | O-n-C₅H₁₁ | n-C₃H₇ |
| 620, | 725, | 830, | 935 | O-n-C₅H₁₁ | n-C₄H₉ |
| 621, | 726, | 831, | 936 | O-n-C₅H₁₁ | n-C₅H₁₁ |
| 622, | 727, | 832, | 937 | O-n-C₅H₁₁ | n-C₆H₁₃ |
| 623, | 728, | 833, | 938 | O-n-C₅H₁₁ | n-C₇H₁₅ |
| 624, | 729, | 834, | 939 | O-n-C₆H₁₃ | CH₃ |
| 625, | 730, | 835, | 940 | O-n-C₆H₁₃ | C₂H₅ |
| 626, | 731, | 836, | 941 | O-n-C₆H₁₃ | n-C₃H₇ |
| 627, | 732, | 837, | 942 | O-n-C₆H₁₃ | n-C₄H₉ |
| 628, | 733, | 838, | 943 | O-n-C₆H₁₃ | n-C₅H₁₁ |
| 629, | 734, | 839, | 944 | O-n-C₆H₁₃ | n-C₆H₁₃ |
| 630, | 735, | 840, | 945 | O-n-C₆H₁₃ | n-C₇H₁₅ |
| 631, | 736, | 841, | 946 | O-n-C₇H₁₅ | CH₃ |
| 632, | 737, | 842, | 947 | O-n-C₇H₁₅ | C₂H₅ |
| 633, | 738, | 843, | 948 | O-n-C₇H₁₅ | n-C₃H₇ |
| 634, | 739, | 844, | 949 | O-n-C₇H₁₅ | n-C₄H₉ |
| 635, | 740, | 845, | 950 | O-n-C₇H₁₅ | n-C₅H₁₁ |
| 636, | 741, | 846, | 951 | O-n-C₇H₁₅ | n-C₆H₁₃ |
| 637, | 742, | 847, | 952 | O-n-C₇H₁₅ | n-C₇H₁₅ |

The following are prepared analogously to Example C:

Example 953-1057

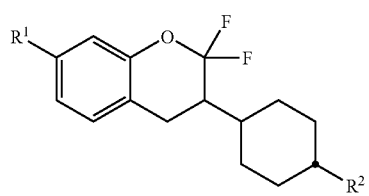

Example 1058-1162

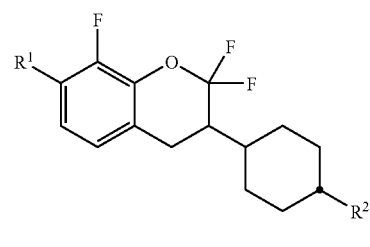

Example 1163-1267

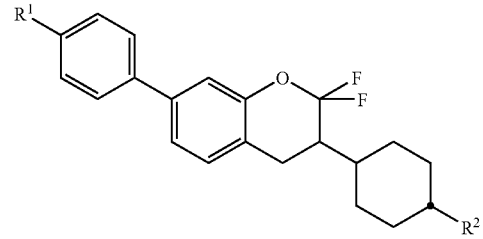

Example 1268-1372

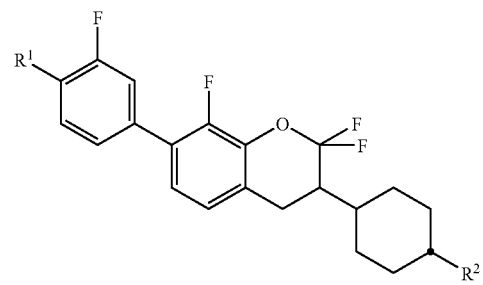

Example 1373-1477

| Example No. | | | | | R¹ | R² |
|---|---|---|---|---|---|---|
| 953, | 1058, | 1163, | 1268, | 1373 | H | CH₃ |
| 954, | 1059, | 1164, | 1269, | 1374 | H | C₂H₅ |
| 955, | 1060, | 1165, | 1270, | 1375 | H | n-C₃H₇ |
| 956, | 1061, | 1166, | 1271, | 1376 | H | n-C₄H₉ |
| 957, | 1062, | 1167, | 1272, | 1377 | H | n-C₅H₁₁ |
| 958, | 1063, | 1168, | 1273, | 1378 | H | n-C₆H₁₃ |
| 959, | 1064, | 1169, | 1274, | 1379 | H | n-C₇H₁₅ |
| 960, | 1065, | 1170, | 1275, | 1380 | CH₃ | CH₃ |
| 961, | 1066, | 1171, | 1276, | 1381 | CH₃ | C₂H₅ |
| 962, | 1067, | 1172, | 1277, | 1382 | CH₃ | n-C₃H₇ |
| 963, | 1068, | 1173, | 1278, | 1383 | CH₃ | n-C₄H₉ |
| 964, | 1069, | 1174, | 1279, | 1384 | CH₃ | n-C₅H₁₁ |
| 965, | 1070, | 1175, | 1280, | 1385 | CH₃ | n-C₆H₁₃ |
| 966, | 1071, | 1176, | 1281, | 1386 | CH₃ | n-C₇H₁₅ |
| 967, | 1072, | 1177, | 1282, | 1387 | C₂H₅ | CH₃ |
| 968, | 1073, | 1178, | 1283, | 1388 | C₂H₅ | C₂H₅ |

| Example No. | | | | | $R^1$ | $R^2$ |
|---|---|---|---|---|---|---|
| 969, | 1074, | 1179, | 1284, | 1389 | $C_2H_5$ | $n-C_3H_7$ |
| 970, | 1075, | 1180, | 1285, | 1390 | $C_2H_5$ | $n-C_4H_9$ |
| 971, | 1076, | 1181, | 1286, | 1391 | $C_2H_5$ | $n-C_5H_{11}$ |
| 972, | 1077, | 1182, | 1287, | 1392 | $C_2H_5$ | $n-C_6H_{13}$ |
| 973, | 1078, | 1183, | 1288, | 1393 | $C_2H_5$ | $n-C_7H_{15}$ |
| 974, | 1079, | 1184, | 1289, | 1394 | $n-C_3H_7$ | $CH_3$ |
| 975, | 1080, | 1185, | 1290, | 1395 | $n-C_3H_7$ | $C_2H_5$ |
| 976, | 1081, | 1186, | 1291, | 1396 | $n-C_3H_7$ | $n-C_3H_7$ |
| 977, | 1082, | 1187, | 1292, | 1397 | $n-C_3H_7$ | $n-C_4H_9$ |
| 978, | 1083, | 1188, | 1293, | 1398 | $n-C_3H_7$ | $n-C_5H_{11}$ |
| 979, | 1084, | 1189, | 1294, | 1399 | $n-C_3H_7$ | $n-C_6H_{13}$ |
| 980, | 1085, | 1190, | 1295, | 1400 | $n-C_3H_7$ | $n-C_7H_{15}$ |
| 981, | 1086, | 1191, | 1296, | 1401 | $n-C_4H_9$ | $CH_3$ |
| 982, | 1087, | 1192, | 1297, | 1402 | $n-C_4H_9$ | $C_2H_5$ |
| 983, | 1088, | 1193, | 1298, | 1403 | $n-C_4H_9$ | $n-C_3H_7$ |
| 984, | 1089, | 1194, | 1299, | 1404 | $n-C_4H_9$ | $n-C_4H_9$ |
| 985, | 1090, | 1195, | 1300, | 1405 | $n-C_4H_9$ | $n-C_5H_{11}$ |
| 986, | 1091, | 1196, | 1301, | 1406 | $n-C_4H_9$ | $n-C_6H_{13}$ |
| 987, | 1092, | 1197, | 1302, | 1407 | $n-C_4H_9$ | $n-C_7H_{15}$ |
| 988, | 1093, | 1198, | 1303, | 1408 | $n-C_5H_{11}$ | $CH_3$ |
| 989, | 1094, | 1199, | 1304, | 1409 | $n-C_5H_{11}$ | $C_2H_5$ |
| 990, | 1095, | 1200, | 1305, | 1410 | $n-C_5H_{11}$ | $n-C_3H_7$ |
| 991, | 1096, | 1201, | 1306, | 1411 | $n-C_5H_{11}$ | $n-C_4H_9$ |
| 992, | 1097, | 1202, | 1307, | 1412 | $n-C_5H_{11}$ | $n-C_5H_{11}$ |
| 993, | 1098, | 1203, | 1308, | 1413 | $n-C_5H_{11}$ | $n-C_6H_{13}$ |
| 994, | 1009, | 1204, | 1309, | 1414 | $n-C_5H_{11}$ | $n-C_7H_{15}$ |
| 995, | 1199, | 1205, | 1310, | 1415 | $n-C_6H_{13}$ | $CH_3$ |
| 996, | 1101, | 1206, | 1311, | 1416 | $n-C_6H_{13}$ | $C_2H_5$ |
| 997, | 1102, | 1207, | 1312, | 1417 | $n-C_6H_{13}$ | $n-C_3H_7$ |
| 998, | 1103, | 1208, | 1313, | 1418 | $n-C_6H_{13}$ | $n-C_4H_9$ |
| 999, | 1104, | 1209, | 1314, | 1419 | $n-C_6H_{13}$ | $n-C_5H_{11}$ |
| 1000, | 1105, | 1210, | 1315, | 1420 | $n-C_6H_{13}$ | $n-C_6H_{13}$ |
| 1001, | 1106, | 1211, | 1316, | 1421 | $n-C_6H_{13}$ | $n-C_7H_{15}$ |
| 1002, | 1107, | 1212, | 1317, | 1422 | $n-C_7H_{15}$ | $CH_3$ |
| 1003, | 1108, | 1213, | 1318, | 1423 | $n-C_7H_{16}$ | $C_2H_5$ |
| 1004, | 1109, | 1214, | 1319, | 1424 | $n-C_7H_{15}$ | $n-C_3H_7$ |
| 1005, | 1110, | 1215, | 1320, | 1425 | $n-C_7H_{15}$ | $n-C_4H_9$ |
| 1006, | 1111, | 1216, | 1321, | 1426 | $n-C_7H_{15}$ | $n-C_5H_{11}$ |
| 1007, | 1112, | 1217, | 1322, | 1427 | $n-C_7H_{15}$ | $n-C_6H_{13}$ |
| 1008, | 1113, | 1218, | 1323, | 1428 | $n-C_7H_{15}$ | $n-C_7H_{15}$ |
| 1009, | 1114, | 1219, | 1324, | 1429 | $OCH_3$ | $CH_3$ |
| 1010, | 1115, | 1220, | 1325, | 1430 | $OCH_3$ | $C_2H_6$ |
| 1011, | 1116, | 1221, | 1326, | 1431 | $OCH_3$ | $n-C_3H_7$ |
| 1012, | 1117, | 1222, | 1327, | 1432 | $OCH_3$ | $n-C_4H_9$ |
| 1013, | 1118, | 1223, | 1328, | 1433 | $OCH_3$ | $n-C_5H_{11}$ |
| 1014, | 1119, | 1224, | 1329, | 1434 | $OCH_3$ | $n-C_6H_{13}$ |
| 1015, | 1120, | 1225, | 1330, | 1435 | $OCH_3$ | $n-C_7H_{15}$ |
| 1016, | 1121, | 1226, | 1331, | 1436 | $OC_2H_5$ | $CH_3$ |
| 1017, | 1122, | 1227, | 1332, | 1437 | $OC_2H_5$ | $C_2H_5$ |
| 1018, | 1123, | 1228, | 1333, | 1438 | $OC_2H_5$ | $n-C_3H_7$ |
| 1019, | 1124, | 1229, | 1334, | 1439 | $OC_2H_5$ | $n-C_4H_9$ |
| 1020, | 1125, | 1230, | 1335, | 1440 | $OC_2H_5$ | $n-C_5H_{11}$ |
| 1021, | 1126, | 1231, | 1336, | 1441 | $OC_2H_5$ | $n-C_6H_{13}$ |
| 1022, | 1127, | 1232, | 1337, | 1442 | $OC_2H_5$ | $n-C_7H_{15}$ |
| 1023, | 1128, | 1233, | 1338, | 1443 | $O-n-C_3H_7$ | $CH_3$ |
| 1024, | 1129, | 1234, | 1339, | 1444 | $O-n-C_3H_7$ | $C_2H_5$ |
| 1025, | 1130, | 1235, | 1340, | 1445 | $O-n-C_3H_7$ | $n-C_3H_7$ |
| 1026, | 1131, | 1236, | 1341, | 1446 | $O-n-C_3H_7$ | $n-C_4H_9$ |
| 1027, | 1132, | 1237, | 1342, | 1447 | $O-n-C_3H_7$ | $n-C_5H_{11}$ |
| 1028, | 1133, | 1238, | 1343, | 1448 | $O-n-C_3H_7$ | $n-C_6H_{13}$ |
| 1029, | 1134, | 1239, | 1344, | 1449 | $O-n-C_3H_7$ | $n-C_7H_{15}$ |
| 1030, | 1135, | 1240, | 1345, | 1450 | $O-n-C_4H_9$ | $CH_3$ |
| 1031, | 1136, | 1241, | 1346, | 1451 | $O-n-C_4H_9$ | $C_2H_5$ |
| 1032, | 1137, | 1242, | 1347, | 1452 | $O-n-C_4H_9$ | $n-C_3H_7$ |
| 1033, | 1138, | 1243, | 1348, | 1453 | $O-n-C_4H_9$ | $n-C_4H_9$ |
| 1034, | 1139, | 1244, | 1349, | 1454 | $O-n-C_4H_9$ | $n-C_5H_{11}$ |
| 1035, | 1140, | 1245, | 1350, | 1455 | $O-n-C_4H_9$ | $n-C_6H_{13}$ |
| 1036, | 1141, | 1246, | 1351, | 1456 | $O-n-C_4H_9$ | $n-C_7H_{15}$ |
| 1037, | 1142, | 1247, | 1352, | 1457 | $O-n-C_5H_{11}$ | $CH_3$ |
| 1038, | 1143, | 1248, | 1353, | 1458 | $O-n-C_5H_{11}$ | $C_2H_5$ |
| 1039, | 1144, | 1249, | 1354, | 1459 | $O-n-C_5H_{11}$ | $n-C_3H_7$ |
| 1040, | 1145, | 1250, | 1355, | 1460 | $O-n-C_5H_{11}$ | $n-C_4H_9$ |
| 1041, | 1146, | 1251, | 1356, | 1461 | $O-n-C_5H_{11}$ | $n-C_5H_{11}$ |
| 1042, | 1147, | 1252, | 1357, | 1462 | $O-n-C_5H_{11}$ | $n-C_6H_{13}$ |
| 1043, | 1148, | 1253, | 1358, | 1463 | $O-n-C_5H_{11}$ | $n-C_7H_{15}$ |
| 1044, | 1149, | 1254, | 1359, | 1464 | $O-n-C_6H_{13}$ | $CH_3$ |
| 1045, | 1150, | 1255, | 1360, | 1465 | $O-n-C_6H_{13}$ | $C_2H_6$ |
| 1046, | 1151, | 1256, | 1361, | 1466 | $O-n-C_6H_{13}$ | $n-C_3H_7$ |
| 1047, | 1152, | 1257, | 1362, | 1467 | $O-n-C_6H_{13}$ | $n-C_4H_9$ |
| 1048, | 1153, | 1258, | 1363, | 1468 | $O-n-C_6H_{13}$ | $n-C_5H_{11}$ |
| 1049, | 1154, | 1259, | 1364, | 1469 | $O-n-C_6H_{13}$ | $n-C_6H_{13}$ |
| 1050, | 1155, | 1260, | 1365, | 1470 | $O-n-C_6H_{13}$ | $n-C_7H_{15}$ |
| 1051, | 1156, | 1261, | 1366, | 1471 | $O-n-C_7H_{16}$ | $CH_3$ |
| 1052, | 1157, | 1262, | 1367, | 1472 | $O-n-C_7H_{15}$ | $C_2H_5$ |
| 1053, | 1158, | 1263, | 1368, | 1473 | $O-n-C_7H_{16}$ | $n-C_3H_7$ |
| 1054, | 1159, | 1264, | 1369, | 1474 | $O-n-C_7H_{15}$ | $n-C_4H_9$ |
| 1055, | 1160, | 1265, | 1370, | 1475 | $O-n-C_7H_{15}$ | $n-C_5H_{11}$ |
| 1056, | 1161, | 1266, | 1371, | 1476 | $O-n-C_7H_{15}$ | $n-C_6H_{13}$ |
| 1057, | 1162, | 1267, | 1372, | 1477 | $O-n-C_7H_{16}$ | $n-C_7H_{15}$ |

The following are prepared analogously to Example C:

Example 1478-1533

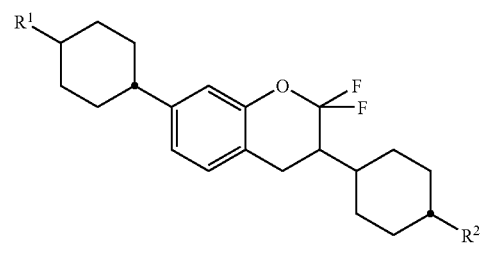

Example 1534-1589

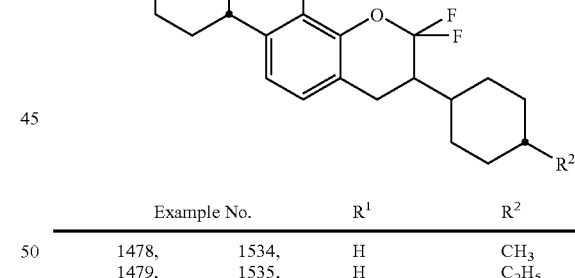

| Example No. | | $R^1$ | $R^2$ |
|---|---|---|---|
| 1478, | 1534, | H | $CH_3$ |
| 1479, | 1535, | H | $C_2H_5$ |
| 1480, | 1536, | H | $n-C_3H_7$ |
| 1481, | 1537, | H | $n-C_4H_9$ |
| 1482, | 1538, | H | $n-C_5H_{11}$ |
| 1483, | 1539, | H | $n-C_6H_{13}$ |
| 1484, | 1540, | H | $n-C_7H_{15}$ |
| 1485, | 1541, | $CH_3$ | $CH_3$ |
| 1486, | 1542, | $CH_3$ | $C_2H_5$ |
| 1487, | 1543, | $CH_3$ | $n-C_3H_7$ |
| 1488, | 1544, | $CH_3$ | $n-C_4H_9$ |
| 1489, | 1545, | $CH_3$ | $n-C_5H_{11}$ |
| 1490, | 1546, | $CH_3$ | $n-C_6H_{13}$ |
| 1491, | 1547, | $CH_3$ | $n-C_7H_{15}$ |
| 1492, | 1548, | $C_2H_5$ | $CH_3$ |
| 1493, | 1549, | $C_2H_5$ | $C_2H_5$ |
| 1494, | 1550, | $C_2H_5$ | $n-C_3H_7$ |
| 1495, | 1551, | $C_2H_5$ | $n-C_4H_9$ |
| 1496, | 1552, | $C_2H_5$ | $n-C_5H_{11}$ |
| 1497, | 1553, | $C_2H_5$ | $n-C_6H_{13}$ |
| 1498, | 1554, | $C_2H_5$ | $n-C_7H_{15}$ |

-continued

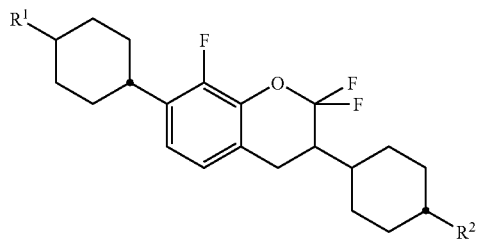

| Example No. | | R¹ | R² |
|---|---|---|---|
| 1499, | 1555, | n-C₃H₇ | CH₃ |
| 1500, | 1556, | n-C₃H₇ | C₂H₅ |
| 1501, | 1557, | n-C₃H₇ | n-C₃H₇ |
| 1502, | 1558, | n-C₃H₇ | n-C₄H₉ |
| 1503, | 1559, | n-C₃H₇ | n-C₅H₁₁ |
| 1504, | 1560, | n-C₃H₇ | n-C₆H₁₃ |
| 1505, | 1561, | n-C₃H₇ | n-C₇H₁₅ |
| 1506, | 1562, | n-C₄H₉ | CH₃ |
| 1507, | 1563, | n-C₄H₉ | C₂H₅ |
| 1508, | 1564, | n-C₄H₉ | n-C₃H₇ |
| 1509, | 1565, | n-C₄H₉ | n-C₄H₉ |
| 1510, | 1566, | n-C₄H₉ | n-C₅H₁₁ |
| 1511, | 1567, | n-C₄H₉ | n-C₆H₁₃ |
| 1512, | 1568, | n-C₄H₉ | n-C₇H₁₅ |
| 1513, | 1569, | n-C₅H₁₁ | CH₃ |
| 1514, | 1570, | n-C₅H₁₁ | C₂H₅ |
| 1515, | 1571, | n-C₅H₁₁ | n-C₃H₇ |
| 1516, | 1572, | n-C₅H₁₁ | n-C₄H₉ |
| 1517, | 1573, | n-C₅H₁₁ | n-C₅H₁₁ |
| 1518, | 1574, | n-C₅H₁₁ | n-C₆H₁₃ |
| 1519, | 1575, | n-C₅H₁₁ | n-C₇H₁₅ |
| 1520, | 1576, | n-C₆H₁₃ | CH₃ |
| 1521, | 1577, | n-C₆H₁₃ | C₂H₅ |
| 1522, | 1578, | n-C₆H₁₃ | n-C₃H₇ |
| 1523, | 1579, | n-C₆H₁₃ | n-C₄H₉ |
| 1524, | 1580, | n-C₆H₁₃ | n-C₅H₁₁ |
| 1525, | 1581, | n-C₆H₁₃ | n-C₆H₁₃ |
| 1526, | 1582, | n-C₆H₁₃ | n-C₇H₁₅ |
| 1527, | 1583, | n-C₇H₁₅ | CH₃ |
| 1528, | 1584, | n-C₇H₁₅ | C₂H₅ |
| 1529, | 1585, | n-C₇H₁₅ | n-C₃H₇ |
| 1530, | 1586, | n-C₇H₁₅ | n-C₄H₉ |
| 1531, | 1587, | n-C₇H₁₅ | n-C₅H₁₁ |
| 1532, | 1588, | n-C₇H₁₅ | n-C₆H₁₃ |
| 1533, | 1589, | n-C₇H₁₅ | n-C₇H₁₅ |

The following are prepared analogously to Example A:

Example 1534-1533

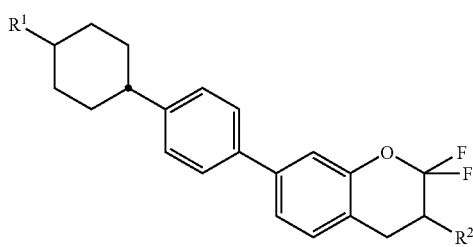

Example 1590-1645

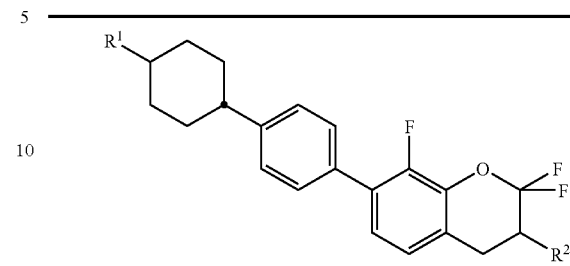

| Example No. | | R¹ | R² |
|---|---|---|---|
| 1534, | 1590, | H | CH₃ |
| 1535, | 1591, | H | C₂H₅ |
| 1536, | 1592, | H | n-C₃H₇ |
| 1537, | 1593, | H | n-C₄H₉ |
| 1538, | 1594, | H | n-C₅H₁₁ |
| 1539, | 1595, | H | n-C₆H₁₃ |
| 1540, | 1596, | H | n-C₇H₁₅ |
| 1541, | 1597, | CH₃ | CH₃ |
| 1542, | 1598, | CH₃ | C₂H₅ |
| 1543, | 1599, | CH₃ | n-C₃H₇ |
| 1544, | 1600, | CH₃ | n-C₄H₉ |
| 1545, | 1601, | CH₃ | n-C₅H₁₁ |
| 1546, | 1602, | CH₃ | n-C₆H₁₃ |
| 1547, | 1603, | CH₃ | n-C₇H₁₅ |
| 1548, | 1604, | C₂H₅ | CH₃ |
| 1549, | 1605, | C₂H₅ | C₂H₅ |
| 1550, | 1606, | C₂H₅ | n-C₃H₇ |
| 1551, | 1607, | C₂H₅ | n-C₄H₉ |
| 1552, | 1608, | C₂H₅ | n-C₅H₁₁ |
| 1553, | 1609, | C₂H₅ | n-C₆H₁₃ |
| 1554, | 1610, | C₂H₅ | n-C₇H₁₅ |
| 1555, | 1611, | n-C₃H₇ | CH₃ |
| 1556, | 1612, | n-C₃H₇ | C₂H₅ |
| 1557, | 1613, | n-C₃H₇ | n-C₃H₇ |
| 1558, | 1614, | n-C₃H₇ | n-C₄H₉ |
| 1559, | 1615, | n-C₃H₇ | n-C₅H₁₁ |
| 1560, | 1616, | n-C₃H₇ | n-C₆H₁₃ |
| 1561, | 1617, | n-C₃H₇ | n-C₇H₁₅ |
| 1562, | 1618, | n-C₄H₉ | CH₃ |
| 1563, | 1619, | n-C₄H₉ | C₂H₅ |
| 1564, | 1620, | n-C₄H₉ | n-C₃H₇ |
| 1565, | 1621, | n-C₄H₉ | n-C₄H₉ |
| 1566, | 1622, | n-C₄H₉ | n-C₅H₁₁ |
| 1567, | 1623, | n-C₄H₉ | n-C₆H₁₃ |
| 1568, | 1624, | n-C₄H₉ | n-C₇H₁₅ |
| 1569, | 1625, | n-C₅H₁₁ | CH₃ |
| 1570, | 1626, | n-C₅H₁₁ | C₂H₅ |
| 1571, | 1627, | n-C₅H₁₁ | n-C₃H₇ |
| 1572, | 1628, | n-C₅H₁₁ | n-C₄H₉ |
| 1573, | 1629, | n-C₅H₁₁ | n-C₅H₁₁ |
| 1574, | 1630, | n-C₅H₁₁ | n-C₆H₁₃ |
| 1575, | 1631, | n-C₅H₁₁ | n-C₇H₁₅ |
| 1576, | 1632, | n-C₆H₁₃ | CH₃ |
| 1577, | 1633, | n-C₆H₁₃ | C₂H₅ |
| 1578, | 1634, | n-C₆H₁₃ | n-C₃H₇ |
| 1579, | 1635, | n-C₆H₁₃ | n-C₄H₉ |
| 1580, | 1636, | n-C₆H₁₃ | n-C₅H₁₁ |
| 1581, | 1637, | n-C₆H₁₃ | n-C₆H₁₃ |
| 1582, | 1638, | n-C₆H₁₃ | n-C₇H₁₅ |
| 1583, | 1639, | n-C₇H₁₅ | CH₃ |
| 1584, | 1640, | n-C₇H₁₅ | C₂H₅ |
| 1585, | 1641, | n-C₇H₁₅ | n-C₃H₇ |
| 1586, | 1642, | n-C₇H₁₅ | n-C₄H₉ |
| 1587, | 1643, | n-C₇H₁₅ | n-C₅H₁₁ |
| 1588, | 1644, | n-C₇H₁₅ | n-C₆H₁₃ |
| 1589, | 1645, | n-C₇H₁₅ | n-C₇H₁₅ |

Measurements for selected Examples:

Example No. 1612

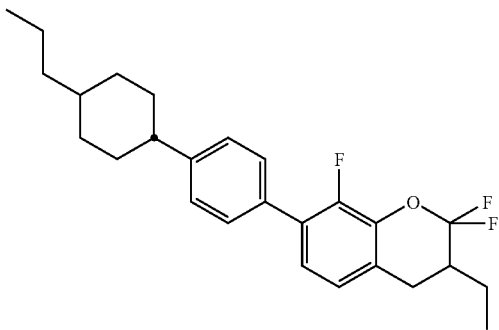

Phase behavior: C 124 I. Δε=−6.6; Δn 0.135.

The invention claimed is:

1. A compound of the general formula I:

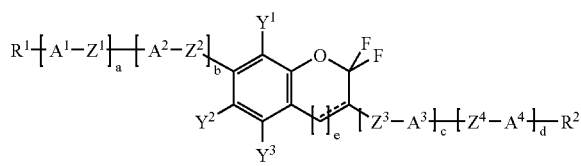

in which:
a, b, c, d and e independently of one another are 0 or 1;
$R^1$ and $R^2$ independently of one another are hydrogen, —F, —Cl, —Br, —I, —CN, —SCN, —NCS, —$SF_5$, an alkanyl, alkoxy, alkenyl or alkynyl having up to 15 carbon atoms, which is unsubstituted, monosubstituted by —CN or —$CF_3$ or monosubstituted or polysubstituted by F, Cl, Br and/or I, where in these radicals one or more $CH_2$ groups can also in each case independently of one another be replaced by —O—, —S—, —$SO_2$—, —CO—, —COO—, —OCO— or —OCO—O—, such that hetero-atoms are not directly linked, or are a polymerizable group P;
$Y^1$ is halogen, halogenated alkyl or halogenated alkoxy having 1-8 carbon atoms,
$Y^2$ and $Y^3$ independently of one another are hydrogen, halogen, halogenated alkyl or halogenated alkoxy having 1 to 8 carbon atoms;
$A^1$, $A^2$, $A^3$ and $A^4$ independently of one another are 1,4-phenylene which can be unsubstituted or mono- to tetrasubstituted independently of one another by —CN, —F, —Cl, —Br, —I, $C_1$-$C_6$-alkanyl which can be unsubstituted or mono- or poly-substituted by fluorine and/or chlorine, or $C_1$-$C_6$-alkoxy which can be unsubstituted or mono- or poly- substituted by fluorine and/or chlorine; 1,4-cyclohexylene, 1,4-cyclohexenylene or 1,4-cyclohexadienylene, in which —$CH_2$— can independently of one another be replaced once or twice by —O— or —S— such that heteroatoms are not directly linked, and which can be unsubstituted or mono- or polysubstituted by —F, —Cl, —Br and/or —I;
$Z^1$, $Z^2$, $Z^3$ and $Z^4$ independently of one another are a single bond, —$CF_2O$—, —$OCF_2$—, —$CH_2CH_2$—, —$CF_2CF_2$—, —$CF_2CH_2$—, —$CH_2CF_2$—, —CFH—CHF—, —(CO)O—, —O(CO)—, —$CH_2O$—, —$OCH_2$—, —CF═CH—, —CH═CF—, —CF═CF—, —CH═CH— or —C≡C—; and
═in the oxygen heterocycle of the formula I is a C—C single bond and, if e is 1, can also be a C═C double bond.

2. A compound as claimed in claim 1, wherein e is 1, and ═is a C—C single bond.

3. A compound as claimed in claim 1, wherein $Y^2$ and $Y^3$ are hydrogen.

4. A compound as claimed in claim 1, wherein $Y^1$ is F, Cl or $CF_3$.

5. A compound as claimed in claim 1, wherein $A^1$, $A^2$, $A^3$ and $A^4$ independently of one another are selected from the group comprising

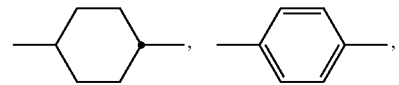

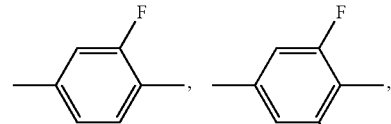

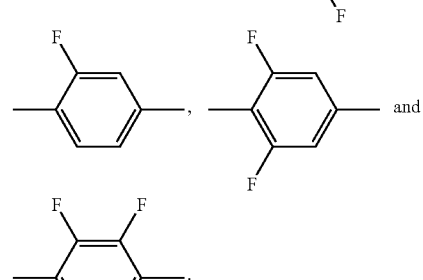

and

6. A compound as claimed in claim 1, wherein $Z^1$, $Z^2$, $Z^3$ and $Z^4$ independently of one another are a single bond, —$CF_2O$— r —$OCF_2$—.

7. A compound as claimed in claim 1, wherein
$R^1$ is hydrogen, fluorine, alkanyl or alkoxy having 1 to 8 carbon atoms; and
$R^2$ is hydrogen, fluorine, alkanyl or alkoxy having 1 to 8 carbon atoms.

8. A compound as claimed in claim 1, wherein a+b+c+d is 1 or 2,
where a +b is 0 or 1 and c+d is 0 or 1.

9. A compound as claimed in claim 2, wherein
a and d are both 0;
b is 0 or 1;
c is 1;
$R^1$, if b is 0, is alkanyl or alkoxy, and if b is 1, is F, alkanyl or alkoxy;
$R^2$ is alkanyl or alkoxy;
$A^2$, if b is 1, is

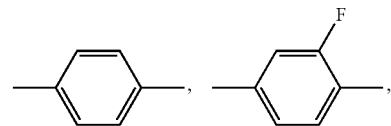

-continued

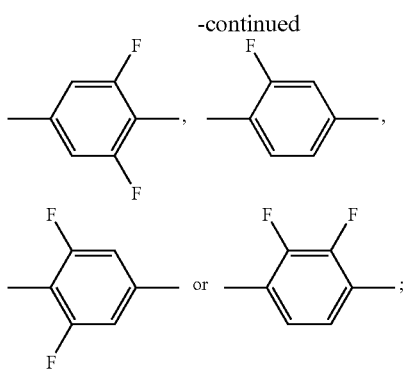

$A^3$ is

$Z^2$, if b is 1, is a single bond; and
$Z^3$ is a single bond.

10. A compound of the general formula II

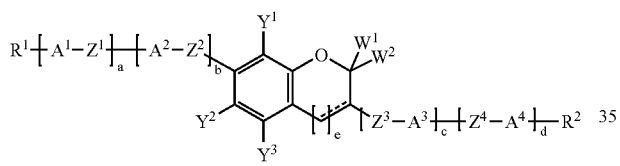

in which
a, b, c, d and e independently of one another are 0 or 1;
$R^1$ is —F, —Cl, —Br, —I, —CN, —SCN, —NCS, —SF$_5$, an alkanyl, alkoxy, alkenyl or alkynyl having up to 15 carbon atoms, which is unsubstituted, monosubstituted by —CN or —CF$_3$ or monosubstituted or polysubstituted by F, Cl, Br and/or I, where in these radicals one or more CH$_2$ groups can also in each case independently of one another be replaced by —O—, —S—, —SO$_2$, —CO—COO—, —OCO— or —OCO—O—, such that hetero-atoms are not directly linked, or are a polymerizable group P;
$R^2$ is hydrogen, —F, —Cl, —Br, —I, —CN, —SCN, —NCS, —SF$_5$, an alkanyl, alkoxy, alkenyl or alkynyl having up to 15 carbon atoms, which is unsubstituted, monosubstituted by —CN or —CF$_3$ or monosubstituted or polysubstituted by F, Cl, Br and/or I, where in these radicals one or more CH$_2$ groups can also in each case independently of one another be replaced by —O—, —S—, —SO$_2$, —, CO—, —COO—, —OCO— or —OCO—O—, such that hetero-atoms are not directly linked, or are a polymerizable group P;
$Y^1$ is F, Cl or CF$_3$,
$Y^2$ and $Y^3$ independently of one another are hydrogen, halogen, halogenated alkyl or halogenated alkoxy having 1 to 8 carbon atoms;
$A^1$, $A^2$, $A^3$ and $A^4$ independently of one another are 1,4-phenylene which can be unsubstituted or mono- to tetrasubstituted independently of one another by —CN, —F, —Cl, —Br, —I, $C_1$-$C_6$-alkanyl which can be unsubstituted or mono- or poly-substituted by fluorine and/or chlorine, or $C_1$-$C_6$-alkoxy which can be unsubstituted or mono- or poly- substituted by fluorine and/or chlorine; 1,4-cyclohexylene, 1,4-cyclohexenylene or 1,4-cyclohexadienylene, in which —CH$_2$— can independently of one another be replaced once or twice by —O— or —S— such that heteroatoms are not directly linked, and which can be unsubstituted or mono- or polysubstituted by —F, —Cl, —Br and/or —I;
$Z^1$, $Z^2$, $Z^3$ and $Z^4$ independently of one another are a single bond, —CF$_2$O—, —OCF$_2$—, —CH$_2$CH$_2$—, —CF$_2$CF$_2$—, —CF$_2$CH$_2$—, —CH$_2$CF$_2$—, —CHF—CHF—, —(CO)O—, —O(CO)—, —CH$_2$O—, —OCH$_2$—, —CF=CH—, —CH=CF—, —CF=CF—, —CH=CH— or —C≡C—; and
═ in the oxygen heterocycle of the formula I is a C—C single bond and, if e is 1, can also be a C=C double bond;
$W^1$ is —SR$^3$ and
$W^2$ is —SR; or
$W^1$ and $W^2$ together are =S or —S—W$^3$—S—, where $R^3$ and $R^4$ independently of one another is alkyl having 1 to 8 carbon atoms; and
$W^3$ is a bivalent organic radical having at least two carbon atoms.

11. A process for the preparation of compounds of the formula I as claimed in claim 1, wherein a compound of the formula II

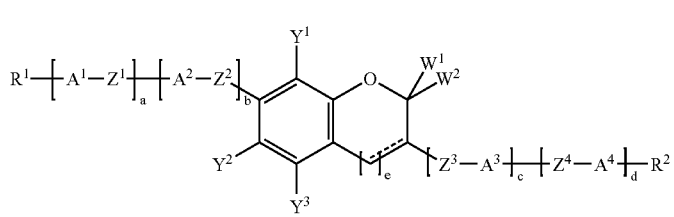

in which a, b, c, d, e, $R^1$, $R^2$, $A^1$, $A^2$, $A^3$, $A^4$, $Y^1$, $Y^2$, $Y^3$, $Z^1$, $Z^2$, $Z^3$, $Z^4$ and ═ are as defined for formula I, $W^1$ is —SR$^3$ and $W^2$ is —SR$^4$ $W^1$ and $W^2$ together are =S or —S—W$^3$—S—, where $R^3$ and $R^4$ independently of one another are alkyl having 1 to 8 carbon atoms; and $W^3$ is a bivalent organic radical having at least two carbon atoms, is reacted with a fluoride-releasing compound in the presence of an oxidant.

12. The process as claimed in claim 11, wherein the fluoride-releasing compound is HF, pyridine-hydrogen fluoride complexes, triethylamine trishydrofluoride (Et$_3$N·3HF) or tetrabutylammonium dihydrogen-trifluoride; and the oxidant is dimethyldibromohydantoin (DBH), N-chlorosuccinimide (NCS), N-bromosuccinimide (NBS), N-iodosuccinimide (NIS), chlorine, bromine, $SO_2$, $Cl_2$, $SO_2ClF$, $NOBF_4$ or chloramine T.

13. The process as claimed in claim 11, wherein the compound of the formula II in which $W^1$ and $W^2$ are $-S-W^3-S-$ and $W^3$ as defined in claim 11, is prepared by reaction of a lactone of the general formula III

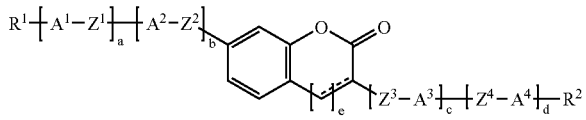

III in which a, b, c, d, e, $R^1$, $R^2$, $A^1$, $A^2$, $A^3$, $A^4$, $Z^1$, $Z^2$, $Z^3$, $Z^4$ and $=$ are as defined for the formulae I and II, with a reagent which is obtainable by reaction of approximately 2 mol equivalents of trialkyl-aluminum with approximately 1 mol equivalent of $HS-W^3-SH$.

14. A liquid crystalline medium having at least two liquid crystalline compounds, comprising at least one compound of formula I as claimed in claim 1.

15. An electrooptical display element, comprising a liquid crystalline medium as claimed in claim 14.

\* \* \* \* \*

UNITED STATES PATENT AND TRADEMARK OFFICE
CERTIFICATE OF CORRECTION

PATENT NO. : 7,648,742 B2
APPLICATION NO. : 11/572759
DATED : January 19, 2010
INVENTOR(S) : Taugerbeck et al.

Page 1 of 1

It is certified that error appears in the above-identified patent and that said Letters Patent is hereby corrected as shown below:

Title Pg, Item (57) Abstract: line 2 reads "b, c, d, e, $R^1$, $R^2$, $A^1$, $A^2$, $A^3$, $A^4$, $Y^1$, $Y^2$, $Y^3$, $Z_1$, $Z^2$, $Z^3$, $Z^4$" should read -- b, c, d, e, $R^1$, $R^2$, $A^1$, $A^2$, $A^3$, $A^4$, $Y^1$, $Y^2$, $Y^3$, $Z^1$, $Z^2$, $Z^3$, $Z^4$ --.

Column 60, line 1 reads "$CF_2CF_2$-, $CF_2CH_2$-, -$CH_2CF_2$-, -CFH-" should read -- $CF_2CF_2$-, $CF_2CH_2$-, -$CH_2CF_2$-, -CHF- --.

Column 60, line 43 reads "-$CF_2$O-r-$OCF_2$-." should read -- -$CF_2$O-or-$OCF_2$- --.

Column 60, line 53 reads "a and dare both 0;" should read -- a and d are both 0; --.

Column 62, line 34 reads "$W^2$ is -SR; or" should read -- $W^2$ is -$SR^4$; or --.

Column 62, line 58 reads "is -$SR^4$ $W^1$ and $W^2$ together are =S or -S-$W^3$-S-," should read -- is -$SR^4$ or $W^1$ and $W^2$ together are =S or -S-$W^3$-S- --.

Column 63, line 6 reads "S- and $W^3$ as defined in claim 11, is prepared by reaction of" should read -- S- and $W^3$ is as defined in claim 11, is prepared by reaction of --.

Signed and Sealed this

Sixth Day of April, 2010

David J. Kappos
*Director of the United States Patent and Trademark Office*